US010736757B2

(12) United States Patent
Saenz Espinoza et al.

(10) Patent No.: US 10,736,757 B2
(45) Date of Patent: Aug. 11, 2020

(54) FITTING SYSTEM

(71) Applicant: ADAPTTECH LIMITED, Birmingham (GB)

(72) Inventors: Mario Saenz Espinoza, Oporto (PT); Frederico Alberto Abreu Carpinteiro, Oporto (PT)

(73) Assignee: ADAPTTECH LIMITED, Birmingham (GB)

( * ) Notice: Subject to any disclaimer, the term of this patent is extended or adjusted under 35 U.S.C. 154(b) by 0 days.

(21) Appl. No.: 16/075,082

(22) PCT Filed: Jan. 15, 2018

(86) PCT No.: PCT/EP2018/050888
§ 371 (c)(1),
(2) Date: Aug. 2, 2018

(87) PCT Pub. No.: WO2018/130691
PCT Pub. Date: Jul. 19, 2018

(65) Prior Publication Data
US 2020/0197195 A1  Jun. 25, 2020

(30) Foreign Application Priority Data

Jan. 13, 2017 (LU) ........................................ 100021

(51) Int. Cl.
G06K 9/00 (2006.01)
A61F 2/76 (2006.01)
A61F 2/80 (2006.01)
A61B 5/00 (2006.01)

(52) U.S. Cl.
CPC .............. *A61F 2/76* (2013.01); *A61B 5/0064* (2013.01); *A61B 5/0073* (2013.01); *A61B 5/0082* (2013.01); *A61B 5/68335* (2017.08); *A61F 2/80* (2013.01); *A61B 2562/029* (2013.01); *A61B 2562/0219* (2013.01); *A61B 2562/0247* (2013.01); *A61B 2562/0271* (2013.01); *A61B 2562/0295* (2013.01); *A61F 2002/7635* (2013.01); *A61F 2002/7665* (2013.01)

(58) Field of Classification Search
None
See application file for complete search history.

(56) References Cited

U.S. PATENT DOCUMENTS 4,745,812 A    5/1988  Amazeen et al.
5,886,775 A *  3/1999  Houser ................ G01S 5/0247
                                                  356/4.01
5,993,400 A   11/1999  Rincoe et al.
(Continued)

FOREIGN PATENT DOCUMENTS

EP    1 935 379 A2   6/2008
EP    2 918 967 A1   6/2015
(Continued)

*Primary Examiner* — Atiba O Fitzpatrick
(74) *Attorney, Agent, or Firm* — 24IP Law Group USA, PLLC; Timothy DeWitt

(57) ABSTRACT

A method and apparatus to scan and measure the surface of objects using a radiation source, such as a laser. When combined with bio-data from bio-sensors to create a profile, the invention is particularly useful for measuring the internal surface of a prosthetic socket and improving the fit between the socket and the residual limb.

16 Claims, 17 Drawing Sheets

(56) References Cited

U.S. PATENT DOCUMENTS

| | | |
|---|---|---|
| 6,177,034 B1 | 1/2001 | Ferrone |
| 6,231,616 B1 | 5/2001 | Helmy |
| 6,287,253 B1 | 9/2001 | Ortega et al. |
| 6,463,351 B1 | 10/2002 | Clynch |
| 6,585,774 B2 | 7/2003 | Dean et al. |
| 6,968,246 B2 | 11/2005 | Watson et al. |
| 7,150,762 B2 | 12/2006 | Caspers |
| 7,655,049 B2 | 2/2010 | Phillips |
| 7,670,386 B2 | 3/2010 | Ezenwa |
| 7,768,656 B2 | 8/2010 | Lapa et al. |
| 7,780,741 B2 | 8/2010 | Janusson et al. |
| 8,142,369 B2 | 3/2012 | Sanders et al. |
| 8,423,167 B2 | 4/2013 | Sanders et al. |
| 8,488,129 B2 | 7/2013 | Lapa |
| 8,758,449 B2 | 6/2014 | Caspers |
| 8,784,340 B2 | 7/2014 | Sanders et al. |
| 9,056,023 B2 | 6/2015 | Sanders et al. |
| 9,072,463 B2 | 7/2015 | Sanders et al. |
| 9,119,735 B2 | 9/2015 | Accini et al. |
| 9,241,812 B2 | 1/2016 | Martin et al. |
| 2006/0184067 A1 | 8/2006 | Clark et al. |
| 2007/0255424 A1 | 11/2007 | Leydet |
| 2009/0067706 A1 | 3/2009 | Lapa |
| 2009/0103783 A1 | 4/2009 | Yukhin |
| 2009/0129031 A1 | 5/2009 | Someya et al. |
| 2010/0023149 A1 | 1/2010 | Sanders et al. |
| 2013/0274896 A1 | 10/2013 | Wang et al. |
| 2014/0149082 A1 | 5/2014 | Sanders et al. |
| 2014/0163697 A1 | 6/2014 | Sanders et al. |
| 2015/0165690 A1* | 6/2015 | Tow .................. B29C 64/393 700/119 |
| 2016/0331563 A1* | 11/2016 | Kane .................. A61F 2/76 |
| 2017/0290685 A1* | 10/2017 | Montez .................. A61F 2/80 |

FOREIGN PATENT DOCUMENTS

| | | |
|---|---|---|
| WO | 92/08175 A | 5/1992 |
| WO | 95/05791 A | 8/1994 |
| WO | 2012/083030 A2 | 6/2012 |
| WO | 2015080991 A1 | 6/2015 |
| WO | 2018098417 A1 | 5/2018 |

* cited by examiner

FITTING SYSTEM

CROSS-REFERENCE TO RELATED APPLICATIONS

This application claims priority to and benefit of Luxembourg Patent Application No. LU 100021 filed on 13 Jan. 2017.

BACKGROUND OF THE INVENTION

Field of the Invention

The present invention relates to improvements in relations to systems, apparatus and methods of measuring and adapting objects for a comfortable engagement with an engaging member, and more particularly to systems, apparatus and methods of measuring, adapting and shaping an object to a body part to ensure a comfortable and functional fit between the object and the body part. Examples of the objects include prostheses and orthoses, for example the fitting of a prostheses to a stump of the residual limb of a wearer.

Description of the Related Art

The fitting and shaping of the socket of an artificial limb (prosthesis) to ensure that the artificial limb is an accurate fit with the stump of the residual limb with which the artificial limb engages is one of the most important parts of or in the formation of a prosthesis, and also one of the most difficult. The socket serves as an interface between the residual limb and the prosthesis, allowing comfortable weight bearing, movement, and balance. The socket therefore has to be shaped to be a perfect fit, with an adequate or desired surface bearing or loading to prevent painful points of contact. Pain and discomfort may occur from pressure, friction, temperature, or any other physical situation caused by an improperly fitted socket or a misaligned prosthesis. It will be appreciated that friction will lead to an increase in temperature and this can be measured by temperature sensors.

At the same time, the socket needs to be sufficiently tight so that during movement the prosthesis is firmly held in place and does not fall off or twist. The prosthesis also needs to be adjustable to take into account that the volume of the residual limb changes over time. For example, in the first few months after amputation, the stump of the residual limb will change in shape due to changes in fat and muscle distribution.

Currently, in order to make a new prosthesis to fit the stump, a mould of the stump is first taken, and the socket of the prosthesis is shaped according to the shape of the mould, and this shaping process is either manual or executed by a machine under computer control, or a combination of both. Once this rough shaping is completed, the shape of the socket is then fine-tuned, usually manually, to create a comfortable fit with the stump. However, prior art methods of fine-tuning of the shape of the socket to create a comfortable fit to a stump are laborious, empirical and time consuming. The shaping process relies fundamentally on verbal feedback from the wearer with regard to how the prosthesis feels, where the prosthesis is rubbing and the like. Small changes are then made, and the fit is tried again. Such communication is, however, often imprecise and very simple, with the patient simply indicating generally where discomfort or pain is occurring on the stump. This is made more difficult by the fact that firstly, the nature of the pain or discomfort is that the pain or discomfort usually does not just occur at the point of contact but in an area around the point of contact, so that locating the issue point precisely is very difficult. Secondly, the patient may have to remove the stump from the socket in order to identify the pain point, and once so removed, the pain will tend to soften, again making it more difficult to accurately identify the actual contact point. Moreover, the trauma or the pathology that led to limb loss may itself have caused nerve displacement, so that the place where pain is felt (pain point) and the actual friction or pressure spot may be in two different locations, or have caused reduced sensitivity, so that the patient is unable to give precise information. Furthermore, the psychological trauma or indeed general reluctance of the patient to provide detailed feedback may lead to incorrect or imprecise information. The phenomenon of "phantom limb pain" is also known that will also affect the information provided to a fitting technician by the patient.

There is therefore a need for a system that is able to provide precise, objective and location-specific information about the fit between a residual limb stump and a prosthetic socket.

In an attempt to improve on the prior art approach, U.S. Published Patent Application No. 2014/0063220 discloses a photo-based fitting system in which the patient's residual limb is photographed from many angles to provide a spatial image of the residual limb and to facilitate the design and construction of the prosthetic socket. However, this approach does not provide any information on the comfort of the fit between the stump and the socket once the socket has been formed, and really only provides an alternative to taking a mould of the stump for the rough forming of the socket. There is no teaching provided as to how to better fine tune to the fit between the stump and the socket.

Similarly, WO 2014/036029 discloses a viewfinder-based system for acquiring data on the stump for which a prosthetics socket needs to be built, but again this does not provide any teaching regarding the fine tuning of the socket to ensure a comfortable fit. It should also be noted that in both cases, the information provided is static and refers to a moment in time, when the photograph was taken and ignores any dynamic data produced during actual continued use of the prosthesis.

U.S. Pat. No. 8,784,340 discloses a further solution to the problem of fitting a prosthetic limb in which a liner is fitted over the stump, the liner having a plurality of pressure sensors embedded therein which are connected to a data acquisition system. However, this solution does not provide any teaching as to how the technician can use the collected data to improve the shape of the socket as the pressure sensors does not provide any precise spatial information which can be used to correlate the pressure data with the shape of the socket. This is made worse by the fact that the liner is fitted to the stump, so at least the liner could only provide information on the shape of the stump rather than the socket, and in any event, due to the nature of the liner and its imprecise fitting, the exact location of the sensors on the stump cannot be ascertained in that system. Finally, in the absence of any adhesive layer or securing mechanism, the liner cannot be prevented from continuously moving, thereby providing incorrect data.

Similarly, U.S. Pat. No. 5,993,400 teaches an apparatus and method for monitoring pressure between the surface of a body part (residual limb) and a contact surface on, for example, a prosthetics socket, a bed or a wheelchair. This apparatus and method employ a plurality of pressure sensors disposed in a matrix array between the contact surface and the body part. The sensors produce analog force signals proportional to pressure, and a monitor receives the analog signals and produces output signals, preferably digital, having pressure data corresponding to the pressure at each sensor. A computer processor receives the output signals from the monitor to create a force profile for the sensor array. The sensors may be scanned as a read event in variety of manners, including periodic, continuous, and triggered scanning. This monitoring apparatus and method is used, for example, to fit prosthetics, to monitor bed-ridden and wheelchair-bound patients, to reduce pain and sores caused by uneven distribution of pressure and to monitor pressure between a cast and a person. The sensors may be mounted on a single sheet or on strips for positioning along the body, and monitoring is accomplished by multiplexing and digitizing the analog force signals.

A number of patent documents are known that teach the design and manufacture of prosthetic sockets using computer aided design. For example, International Patent Application No. WO 2012/083030 teaches above knee (AK) and below the knee (BK) prosthetic sockets and specific manufacturing processes for the production of prosthetic sockets through the automated, computer controlled bi-axial and tri-axial braiding of sockets, over a mold or mandrel made of carved foam, plaster material or wax that is a replica of the patient's truncated limb, and is created by a Computer Aided Design (CAD) file controlling a Numerically Controlled (CNC) machine tool. The prosthetic sockets are manufactured using fibers such as graphite or Kevlar, and high-performance resins, and create a socket which is stronger and lighter weight than conventionally manufactured sockets. Braiding also allows incorporation of woven cloth, tapes and other reinforcements into the braiding process for added strength at selected areas.

U.S. Published Patent Application No. 2010/0023149 teaches a method for evaluating prosthetic sockets (and other objects) which are designed and fabricated with computer aided design and manufacturing software. The shape of the prosthetic socket is accurately scanned and digitized. The scanned data are then compared to either an electronic shape data file, or to the shape of another socket, a positive model of a residual limb (or socket), or a residual limb. Any differences detected during the comparison can then be applied to revise the design or fabrication of the socket, to more accurately achieve a desired shape that properly fits the residual limb of a patient and can be used to solve the inverse problem by correcting for observed errors of a specific fabricator before the prosthetic socket is produced. The digitizing process is implemented using a stylus ball that contacts a surface of the socket to produce data indicating the three-dimensional shape of the socket.

SUMMARY OF THE INVENTION

There is accordingly a need for a system and method for improving the fine tuning of the shape of the socket to fit the stump by providing precise information on the mismatching between the shape of the socket and the shape of the stump. More generally, the system and method can be used for identifying difference in shape, load and biosensor profile distribution, as well as the physical characteristics between an object and a body part, i.e. part of a human body, which is engageable with the object.

According to a first aspect of the present invention, there is provided a method of identifying the differences in shape and physical contact characteristics between the object and the body part which is engageable in the object, comprising the steps of scanning the object with a radiation source, such as, but not limited to, a laser, in order to produce a surface map of the object, attaching a plurality of bio-sensors to a surface of the object at locations which are known relative to a reference point, engaging the body part in the object, collecting data from the bio-sensors to record information on the engagement between the body part and the object over the surface of the object, and superimposing the data from the bio-sensors over the surface map of the interior of the object in order to identify areas of the object which need to be adjusted in order to improve the fit of the body part in the object.

The present invention further comprises an apparatus for identifying the differences in shape and physical contact characteristics at an interface between an object and a body part which is engageable in the object, comprising a conical laser assembly and a capturing element for scanning the surface of the object in order to produce a surface map thereof, an adjuster for varying the distance of the laser from the surface, a plurality of bio-sensors attachable to the surface of the object at locations which are known relative to a reference point, data collecting means connected to the bio-sensors for collecting contact data from the plurality of the bio-sensors, processing means for superimposing the bio-sensor data onto the surface map to produce a bio-data profile of the object, and a display for displaying the bio-data profile to a technician.

It will be noted that the bio-sensors may also be attached to the body part but what is important is that they are firmly positioned and held in place between the object and the body part.

Bio-sensors can be of different types and include, but not limited to, one or more of pressure sensors, temperature sensor, accelerometers, magnetometers, pedometers, galvanic response sensors, humidity sensors, air flow sensors, electromyography sensors, electrocardiography sensors, oximetry sensors and mechanomyography sensors. Preferably the sensors include a plurality of pressure and temperature sensors. The pressure sensors measure forces at the normal to the surface of the body part, whilst the temperature sensors indicate friction between the body part and the object due to transverse forces along the surface of the body part.

The body parts can be, for example, a stump of an amputated limb, a limb, a bottom sitting on a wheelchair, a back lying on a bed. The objects are in these examples a socket for a prosthesis, an orthotic element, e.g. knee brace, a wheelchair, or a bed. It will be appreciated that the invention has other applications.

A method and apparatus according to the invention has the advantage that by mapping the bio-data onto the socket surface map, the prosthesis fitting technician is provided with an accurate guide of where issues exist at the interface between the stump and the socket, and therefore makes identification of the regions of the socket which need adapting, rectifying, tuning or shaping and the amount required thereof much easier. As a result, the number of iterations to achieve a good fit is reduced resulting in a shorter, more efficient, and more economic prosthesis fitting process. The method and apparatus of the present invention reduce the cost of fitting a new or replacement prosthetic socket, as well as for adjusting existing prosthetic sockets, and achieve comfort for the patient much more quickly.

In a particularly preferred embodiment, a plurality of temperature and pressure sensors are provided on the socket surface for collecting both temperature and pressure data relating to the engagement between the socket and the stump. The use of both temperature and pressure sensors in the stump allows an improved understanding of the engagement between the stump and the socket to be formed, the temperature sensors providing not only biometric information relating to the surface of the stump but also allows temperature compensation of the pressure readings to be carried out, thereby improving their accuracy, as well as other benefits such as obtaining information about sensitive spots which are prone to ulcers and injury.

The sensors may be attached individually to the socket, it being important primarily that the exact location of each sensor in the socket, relative to a reference point, is known. Preferably, however, the sensors are provided in strips or arrays, so that they may be applied to the surface of the socket in a fixed relation to each other. This has the advantage of making the application process quicker whilst at the same time ensuring accurate spacing. Furthermore, by providing the sensors in strips rather than in a web or net, the spacing between the strips can be varied to control the density of the monitoring, so that high resolution monitoring can be carried out in areas of greater interest, namely with respect to pressure or temperature variation. An appropriate pattern of sensors on or in the strip may be used, such as alternating between pressure and temperature sensors, or indeed any other bio-sensor capable of sensing and measuring a physiological or physical variable of interest.

The radiation source is preferably a conical laser assembly which comprises a laser and an optical element which converts the single laser beam into a two-dimensional laser array. In one embodiment, the laser may one of the type which is made by Coherent of Wilsonville, USA, and sold under part number M203450073, and the optical element is a conical mirror such as that made by Edmund Optics Inc., of Birmingham, USA and sold under model number R5000095826-14015. By focusing the laser beam on the vertex of the conical mirror, the laser beam is converted into a laser line projected from the plane of the base of the conical mirror. This arrangement has the advantage of keeping a fixed distance between the laser and the conical mirror projecting the laser plane at 90 degrees, such that the distance between the place of the laser plane and a capturing element is always known, thereby allowing a stable calibration rule capable of accurately converting pixels to millimetres. This calibration makes it easier to get the real dimensions of the analysed object, but it requires a very precise alignment between the two elements in order to obtain the best results. Such precise alignment is costly to achieve and may also become altered under the everyday-use conditions of a prosthesis clinic, thereby requiring frequent and costly calibration.

In an alternative embodiment, the optical element in the conical laser assembly is a diffractive optical element which converts the laser beam or dot into a variety of patterns, including a conical shape which produces a solid (substantially circular or elliptical) projected laser line with a certain aperture angle. A suitable laser and laser head is made by Laser Components, from Olching Germany and sold under model numbers FP-DOE-520-3-P-268-F300 and FP-DOE-635-3-P-268-F150. This embodiment has the advantage that it is much easier to use and requires less space to mount. However, it requires a dynamic calibration rule to be able to know the real dimensions of the analysed object, because the distance of the projected laser line place will depend on the diameter of the scanned object.

The laser is used in conjunction with a capturing element, for example one or more cameras, which detect and segment the laser on the surface of the socket and accurately measures the distance between the capturing element and each point on the surface. The capturing element is preferably arranged in a fixed position relative to the laser, the distance from the laser being known. The relative position between the source and the capturing element is known and therefore the distance and direction to each point on the surface can be accurately calculated and mapped.

In order to scan the surface of the object, the laser, the conical laser assembly and the capturing element(s) are moved as a single unit towards and away from the surface of the scanned object (i.e. the socket) in order to change the projection of the laser on the surface. This movement changes the part of the surface which is being illuminated, in the case of the prosthetic the projection of the (substantially circular or elliptical) laser line or pattern on the inner surface, and therefore the area that is analysed by the capturing element. The movement is varied to enable the whole surface of the scanned object to be mapped.

The projected laser line or pattern of laser light is projected onto the surface the scanned object with the laser at a first distance from that surface. If any deviations in the height of the surface, however, either in the form of recesses or projections, will cause the distance of the affected points from the laser to change and hence, due to the divergence of the laser, will cause distortions in the circular/elliptical form of the projected laser line raised portions on the surface will cause distortions inwards towards the inner portion of the projected laser line and recessed points will cause distortions outwards of the projected laser line.

By knowing the resolution of the capturing element, after segmenting the projected laser line in the image acquired (intersection of the laser plane with the surface of the object) and detecting a reference point of this projected laser line, it is possible to know the distance in pixels between each point of the projected laser line and a reference point, as is described in more detail below. The reference point could be, for example, a central point if the projected laser line is substantially circular. By determining the distance between the camera and the plane of the projected laser line it is possible to establish a correlation between the virtual dimension in pixels and the real dimension in millimetres. By computing the distance between each pixel of the laser line, and the reference point of the projected laser line, it is possible to obtain the position of each point of the projected laser line which is projected on, and therefore corresponds to, a point on the surface of the socket. After the system calibration (to infer the real position of the points), by joining the information resulting from the analysis of all the images acquired in the x and y dimensions along the z axis it is possible to reconstruct the 3D model of the scanned object, such as the socket.

The apparatus of the invention is capable of fully scanning an internal cylinder with 50 cm height in 30 to 60 seconds. This is a significant improvement of 4 (Rodin4D ECHO) to 20 (Coordinate Measuring Machines—CMM) times faster regarding other solutions available, when considering the same resolution. Furthermore, the apparatus presents a lower complexity, using only one axis of movement to achieve an equivalent resolution to other solutions designed for the same purpose. Only CMM machines of very high complexity are able to reach a higher precision but require a much longer scanning time.

The bio-sensors used in the present system collect bio-data from the prosthesis socket in use. The bio-sensors are thin, preferably less than 1 mm in thickness so that they themselves do not become a source of discomfort for the user and have an impact on data acquisition. Suitable models are available from Interlink Electronics Inc. of California, USA, reference FSR400. This particular model can measure applied force from 0.2N to 20 N and is particularly suited to pressure determination between the stump and the socket. In addition, these bio-sensors can measure resistances from 45Ω to 45 MΩ and vary proportionally according to the force applied over the sensing area (19.635 mm$^2$ approximately). Other useful models include FSR400 Short from Interlink Electronics or HD-001 from IEE in Luxembourg.

Bio-sensors can also be temperature sensors, they too are mechanical transducers and are named Thermistors. Useful thermistor resistances range from 0.4 1Ω to 400 kΩ and they vary according to the temperature to which they are exposed. Suitable sensors such as NTC JT Thermistors, specifically 103 JT-025 are produced by Semitec USA Corp (California, USA).

Depending on the variable of interest, different type of sensors may be used. The preferred embodiment includes a sandwich-type construction, the sensors being placed between two layers of material, which can be made of any suitable polymer, flexible, thin film and be delivered in rolls. There can be one plastic film A comprising two sides A1 and A2, which can be coated with a bio-compatible material on side A1 which will be in contact with the stump skin or a liner and which can be coated with an adhesive material on side A2 which will receive the sensors, as well as the power and data leads thereof and hold them it in place. There can be another plastic film B also comprising two sides B1 and B2, which can be optionally coated with an adhesive material on side B1. Side B1 is intended to fit exactly over side A2 of strip A and thereby sandwich the sensors and leads, and side B2 can be coated with an adhesive material or be composed of an adhesive material and it will be applied and adhere to the socket.

This is in the case of the sensors being applied and adhering to the socket. Other variations of the sensors may be built so that they adhere to the stump or the liner and surface finishes shall be modified to that end.

Plastic film rolls A and B are substantially of the same width or about 1.5 cm to 4 cm and several metres in length, for economic manufacturing; they can be cut later to proper length before use. They can be produced in a high-speed, continuous assembly line which will dispense and place the sensors and power and data leads onto side A2 of film roll A. The assembly line will then dispense and precisely place side B1 of film roll B over side A2 of film roll A and press the two films together so as to create a strip of sandwiched sensors and leads. The continuous sensor strip is then cut at appropriate lengths ranging from about 10 cm to 50 cm to produce individual sensor strips for use. Individual sensor strips, comprising one or more individual bio-sensors 819, 919, are then each fitted with a power and data interface device which is glued, clamped or soldered at one of the extremities of the sensor strip to connect with the power and data leads of the sensor, so as to provide power to the sensors and acquire data from them.

It should be noted that the arrangement and combination of surfaces and finishes described above for all four sides of plastic film rolls A and B is not mandatory and that other constructions may be used, provided the bio-sensors 819, 919 sensors are adequately held in place. Indeed, in a further embodiment the sensor strip could comprise a single plastic film strip, and the sensors and the leads could be treated with an adhesive finish on one side so that proper adhesion to the plastic film would be ensured by the sensors and leads themselves. In this construction, the side of the plastic film facing the socket would have an adhesive finish and the other side facing the stump or liner would have bio-compatible properties. The adhesive is "weak" so that the bio-sensor strip can be removed from one object and re-used on another object. Processes to manufacture bio-sensors in strips or in rolls is achievable through existing know-how and equipment to the persons skilled in the art.

In the fields of science, engineering and statistics, the accuracy of a measurement system is the degree of closeness of measurements of a quantity to that quantity's true value. The precision of a measurement system, related to reproducibility and repeatability, is the degree to which repeated measurements under unchanged conditions show the same results. Measurement resolution is the smallest change in the underlying physical quantity that produces a response in the measurement. In the present case, the measuring resolution of the system is directly related to the camera resolution, the movement resolution, (itself dependent on the motor step and the screw resolution), and the thickness of the projected laser line. The higher the camera and the movement resolutions, and the lower the thickness of the projected laser line, the higher the system resolution as a whole will be.

According to a still further aspect of the present invention, there is provided an apparatus for mapping a three dimensional surface comprising a laser, an optical element located in front of the element through which the beam of the laser passes so as to convert the laser point into the projected laser line when projected onto a surface, a capturing device located in a fixed and known position relative to the laser, means for varying the distance of the laser and capturing element from the surface of the scanned object in order to vary the size of the laser beam and the projected laser line and hence vary the part of the surface illuminated thereby, and processing means for analysing the data from the capturing means in order to determine, in use, the distance between the capturing means and the plane of the projected laser line. This then allows to establish a correlation between the virtual dimension in pixels and the real dimensions in millimetres and thereby generate a three-dimensional map of the surface of the scanned object.

The present invention still further provides a method of mapping a three dimension surface comprising the steps of directing a beam from a radiation source, such as, but not limited to, a laser, through an optical element in order to produce a solid substantially circular projected radiation line or pattern, e.g. cone, on the surface of a scanned object, viewing the surface with one or more capturing elements, such as a camera, which is located in a fixed and known position relative to the radiation source, using the capturing element to measure the distance in pixels between each point of the projected radiation pattern and the reference point, repeating the measurement at different distances of the laser from the surface so that different points on the surface are illuminated until the complete surface has been measured to the required resolution, computing the distance between each pixel of the projected radiation and the reference point in order to obtain the position of each point of the projected radiation, using calibration data in order to convert the measurements in pixels into actual distance measurements, and collating the data collected at the different distances of the radiation light from the surface in order to locate the position of the bio-sensors and to produce a 3D model of the surface of the scanned object.

Preferably, the surface model generated according to any aspect of the invention is displayed to a user such as a prosthesis technician using a three-dimensional display system such as a virtual reality headset, an augmented reality mobile device or the like. Advantageously, the surface may have projected on the display a grid which is calibrated to the socket surface map generated by a computer from the projected laser light and camera(s) data, so as to enable a user easily to correlate the actual surface of the scanned object with the computer-calculated virtual surface and hence easily identify on the real surface the areas which need to be improved, adjusted, tuned or shaped based on the bio-sensor information.

In addition to generating surface maps of sockets as set out above, variations of the apparatus according to the second aspect of the invention may be used to generate a surface map of any three-dimensional surface and could be used not only to analyse irregular surfaces but also changes to regular surfaces in many other and diverse applications, such as pipe inspection in order to identify corrosion or residue, vein inspection for atherosclerosis and aneurysms or the like.

BRIEF DESCRIPTION OF THE DRAWINGS

In order that the invention may be well understood, there will now be described some embodiments thereof, given by way of example, reference being made to the accompanying drawings, in which.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Referring first to FIGS. 1A to 1E, there is shown a summary of the steps involved in mapping and modelling in three dimensions of a socket for an artificial limb. Reference is also made to FIGS. 2 to 4 which shows the apparatus used for the mapping and modelling of the socket in three dimensions. The description below assumes that a laser is used as the radiation source, but it will be appreciated that other beams of light could be used to scan the socket of the artificial limb and this application is not limited to laser scanning.

Figure 1A:
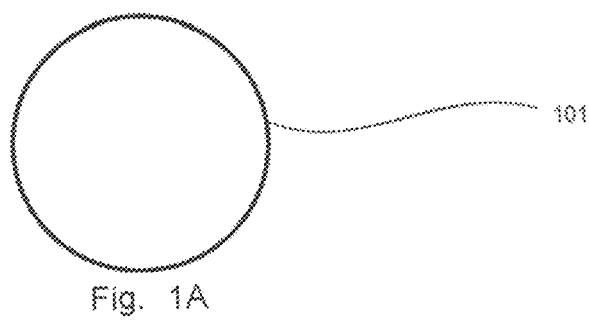
FIGS. 1A to 1E are a conceptual representation of the invention where it relates to socket surface acquisition, measurement and rendering.
Figure 1B:
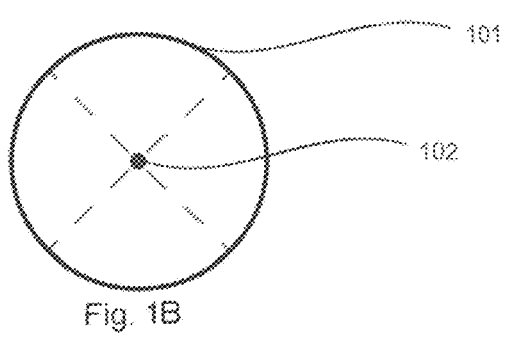
Figure 1C:
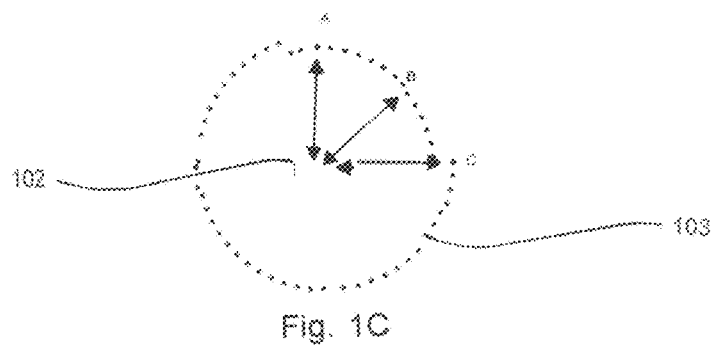
Figure 2:
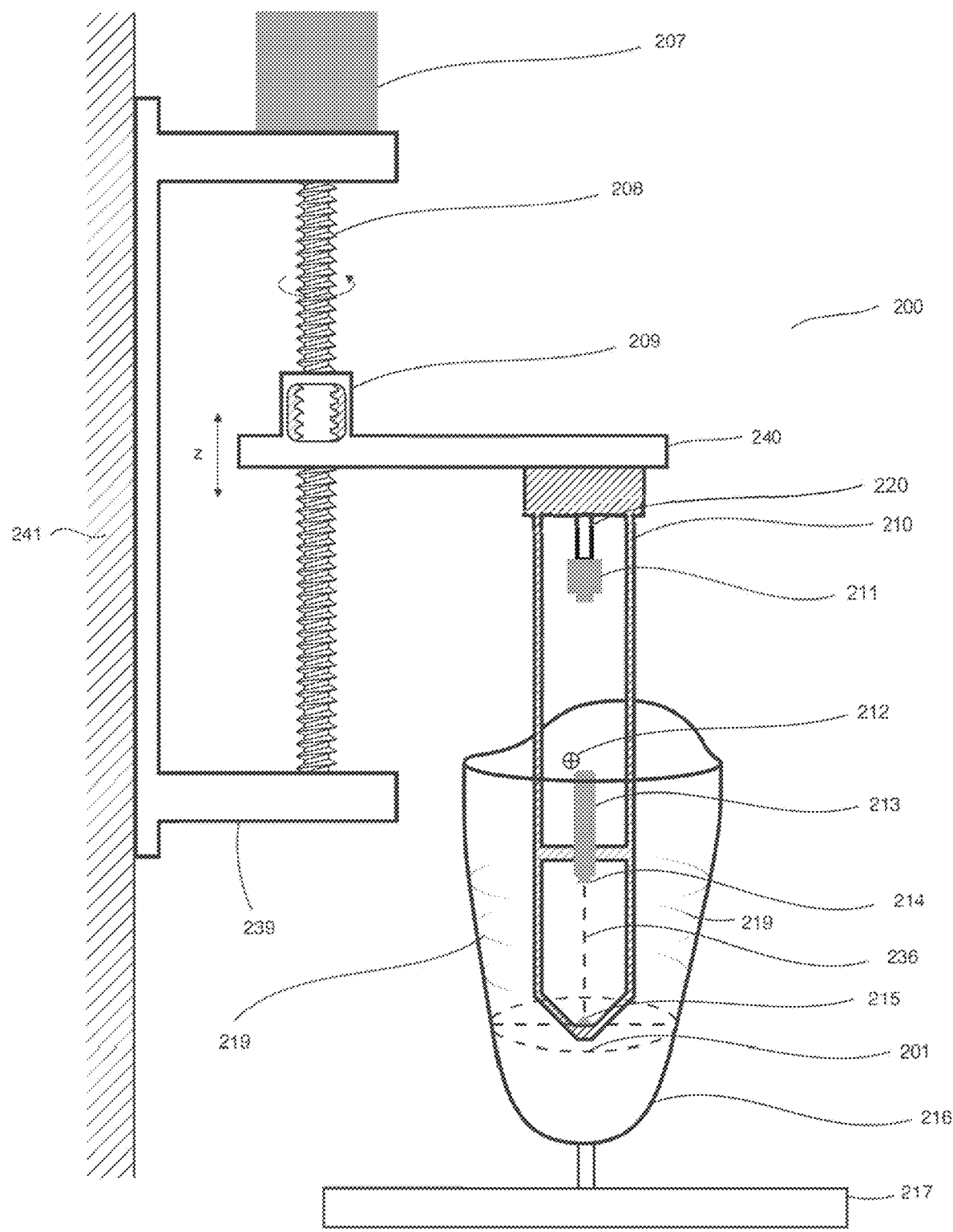
FIG. 2 is a view of the first aspect of the laser and camera system.

FIG. 1A shows a projected laser line 101, as it is projected on the surface of a scanned object. FIG. 1B shows the reference point 102 of the projected laser line 101. In this aspect, the projected laser line 101 is substantially circular in form and the reference point is the centre of the circle, as the centre is computed from data acquired by one or more cameras 411, 511 (see FIGS. 4, 5A and 5B) in a subsequent step. It will be appreciated that the projected laser line 101 may not be circular (or elliptical) in other aspects and, in this case, a suitable reference point needs to be found and used. FIG. 1C shows the projected laser line 101 segmented into discrete data points 103 following identification of the projected laser line 101 by the camera 211. This results in a complete conversion of the projected laser line 101 into a plurality of individual pixels 103, of which A, B and C are representations. By knowing the resolution of the camera 411 and its position relative to the laser beam, by calculating the position of all of the plurality of the line pixels 103, by calibrating the system to infer the real position of each point, the distance of each data point 103 of the line 101 to the reference point 102 may be calculated, and thus position and spatial coordinates of the data points 103 can be determined. These data points 103 will also represent the actual surface of the scanned object.

Figure 1D:
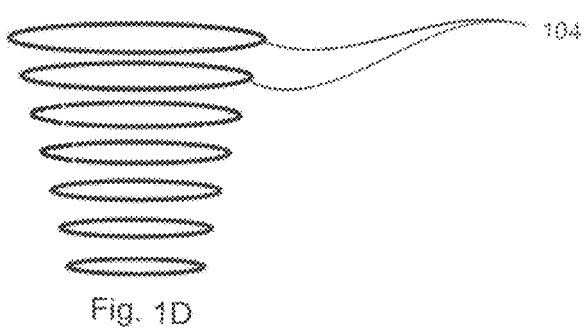
Figure 1E:
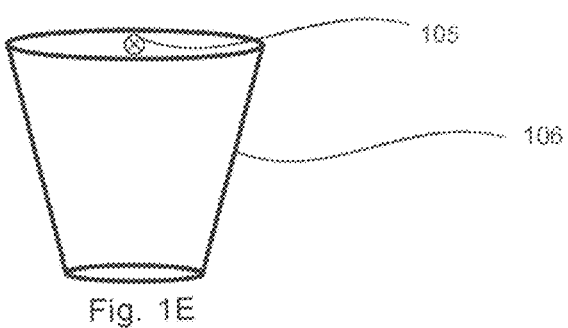

In FIG. 1D, as the camera 211 and laser assembly move together in incremental steps along the z axis, scanning a new area of the socket, variations in the surface dimensions of the socket will result in a corresponding change in the projected laser line 104*a-g* being projected thereon. As the projected laser line acquisition, segmentation, pixel conversion and distance-to-reference point process is repeated across the entire depth of the scanned object, this results in a plurality of virtual substantially projected laser lines 104, which are then joined, as shown in FIG. 1E, to generate a virtual surface map 106 of the scanned object. FIG. 1E also shows a circled x ⊗ 105 which represents origin coordinates on the virtual surface map 106 of the scanned object. The circled x as the origin coordinates 105 will be used as a spatial reference point to allow correct alignment with the origin coordinates 105 of a bio-data map at the final stage of the process.

In FIG. 2, there is shown a schematic illustration of a conical laser assembly 200 according to a first aspect of the invention. There is a moving support assembly 240 which supports a devices support frame 210 and the devices support frame 210 moves with the moving support assembly 240. The devices support frame 210 supports a camera 211, a laser device 213 provided with a laser lens 214 and a conical mirror 215. The moving support assembly 240 is connected to a linear screw 208 by a bushing 209 so as to be moveable towards and away (more frequently vertically) along the longitudinal axis of the scanned socket 216. The linear screw 208 and moving support assembly 240 are secured to an anchor frame 239 which will be attached to a solid, immovable surface or point such as a wall or an appropriate apparatus housing. The linear screw 208 is attached to a motor 207 mounted on the anchor frame 239. The motor 207 rotates the linear screw 208, leading to a movement of the bushing 209 and consequently of all the moving support assembly 240 of all elements (210, 213, 211, 215) connected thereto.

The camera 211 is mounted above a single point laser device 213 which projects a conventional laser beam 236 onto a conical mirror 215. The laser 213 is arranged to focus the laser beam 236 on the vertex of the conical mirror 215, and the mirror surface of the conical mirror 215 reflects the laser beam 236 outwards from the plane of the base of the mirror 215 so as to project the laser line 201 extending from the plane of the base of the mirror 215. The scanned object, a prosthetic socket 216, is mounted on a fixing base 217 which does not move so that the scanned object remains stationary. A physical origin coordinate 212, identified by a circled cross ⊕ and placed on the surface of the socket 216 provides a spatial reference point which will be useful to orient and align the physical socket 216 with the virtual 3D model of the socket 216 and with the 3D profile of the bio-data.

In use, the devices support frame 210 moves vertically, starting from a top position where the laser 213 focuses its laser beam 236 on the conical mirror 215 and begins to scan the top of the socket 216. A line of laser light, the perimeter of which is represented by points line 201 is projected on the internal area of the socket 216, whereupon the process previously described of laser line acquisition, segmentation, calibration, distance-to-reference point calculation and line coordinates calculation is performed. These data are stored in a computer (not shown) and the motor 207 turns the linear screw 208 which in turn moves the moving support assembly 240 to the next incremental position, thereby lowering the devices support frame 210 one unit of movement (typically in increments of 5 mm, but this is not limiting of the invention). The entire process is repeated again in a new data acquisition stage until the entire socket 216 internal surface is scanned and mapped. At the conclusion of the process the data corresponding to each slice of socket surface is joined and a full 3D map of the lines is formed, thus rendering a virtual image of the socket 216 as previously shown in FIG. 1F.

It will be inferred that there is a blind spot on socket 216 mapping caused by the devices support frame 210, the arms of which will block the field of view of camera 211. In order to acquire the hidden points on the socket 216 surface, this may be achieved by installing a decoupling mechanism (not shown) between the moving support assembly 240 and the devices support frame 210, which will allow the support arms of the devices support frame 210 to rotate sufficiently, for the previously hidden portion of laser plane 201 to become visible to the camera 211 while the camera 211 stays in the same position.

Strips of bio-sensors 219 are arranged on the inside of the socket 216 and will record various biomedical parameters, as explained below. These bio-sensors 219 are described in more detail in connections with FIGS. 8 and 9. Only two bio-sensors 219 are shown on FIG. 2 for simplicity, but in fact the inside surface of the socket 216 will have a much larger number of bio-sensors 219. It will also be realised that the bio-sensors 219 are shown much larger on this FIG. 2 than in real life, as the bio-sensors 219 should not affect the position of the limb in the socket 216. The bio-sensors 219 have target or reference markings on their top surface which are visible to the camera. A light source 220, such as an LED white light, illuminates the inside of the socket 216 and the camera 211 records the position of the bio-sensors 219 using the markings. The camera 211 is moved along the vertical axis and several images are captured. The shape of the markings is known and thus the position of the bio-sensors 219 relative to the vertical axis can be determined. It would also be possible to take images under ambient light.

Figure 3A:
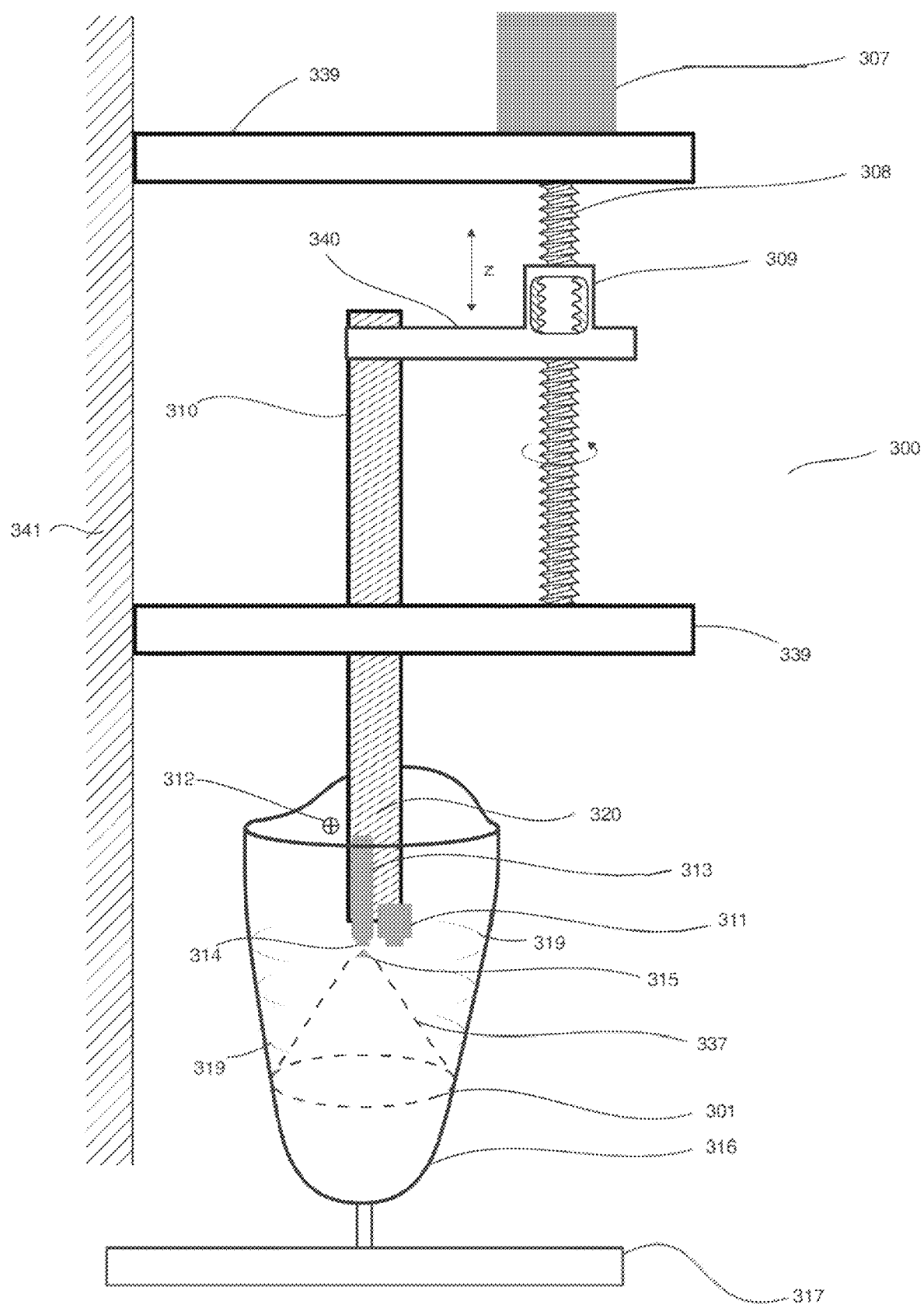
FIG. 3A is a section view of a second aspect of the laser and camera system.
Figure 4:
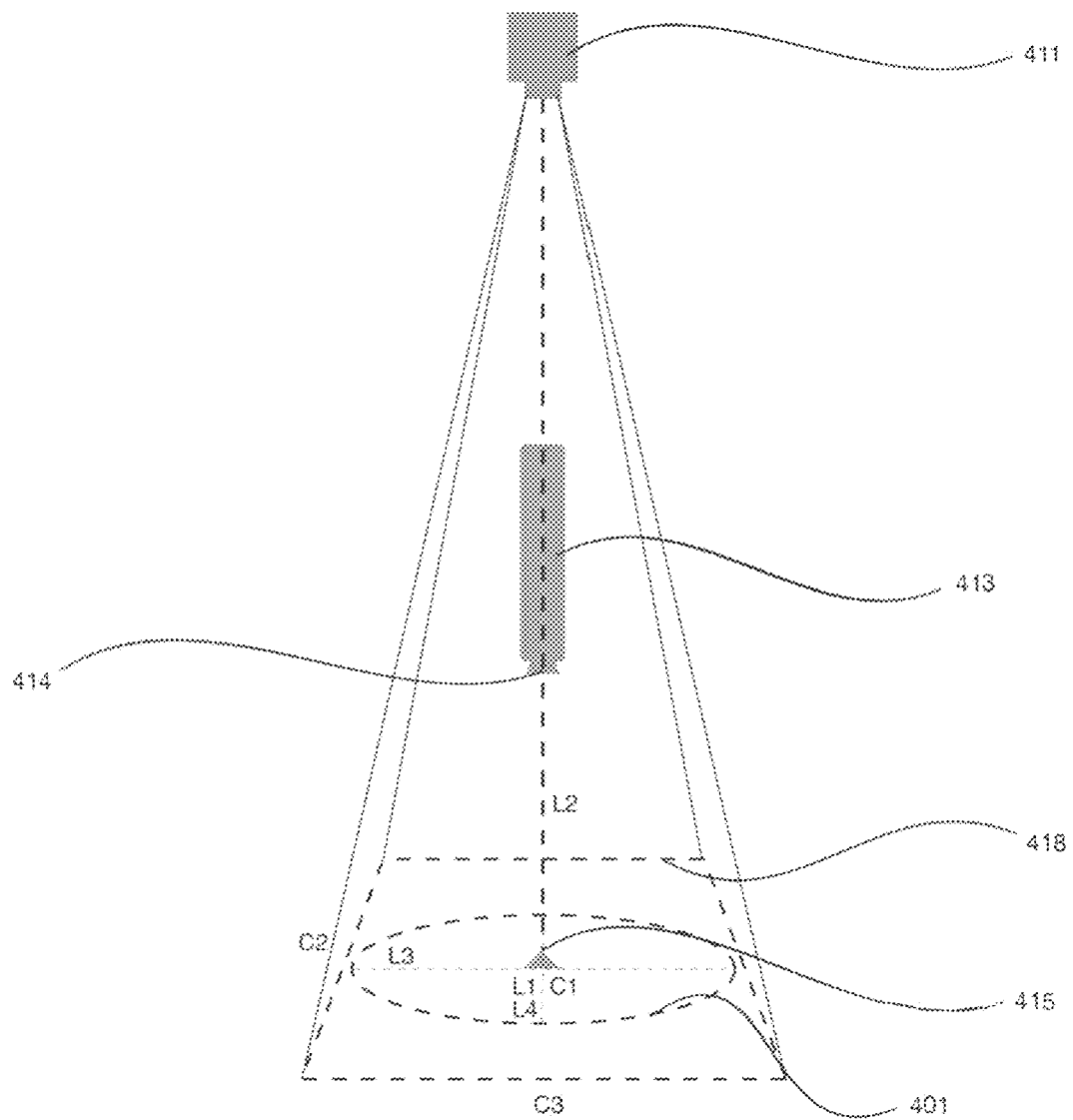
FIG. 4 is a representation of the laser plane and the camera field of view of the first aspect.

FIG. 3A shows a second aspect of the invention which overcomes the blind spot issue discussed above. This second aspect uses the same laser 313 provided with a laser lens 314 which comprises a diffractive optical element 315. When the laser beam from the laser 313 is directed through diffractive optical element 315, the optical element 315 diffracts the projected laser beam 337 and produces a projected solid laser line 301. This is projected outward onto the surface of the scanned socket 316, the diameter and contour of the projected laser line 301 being dependent on the surface of the scanned socket 316.

The laser 313 and the camera 311 are mounted on the device supporting frame 310 that is attached to a moving support assembly 340. The moving support assembly 340 is connected to a linear screw 308 by a bushing 309 so as to be moveable towards and away (more frequently vertically) along the longitudinal axis of the scanned socket 316. The linear screw 308 is attached to the anchor frame 339 which will be attached to a solid, immovable surface or point such as a wall or an appropriate floor-standing apparatus housing 341. The linear screw 308 will be attached to a motor 307, which will rotate the linear screw 308 leading to a movement of the bushing 309 and consequently of the moving support assembly 340 and of all elements (310, 313, 311, 315) connected thereto.

The capturing element in the form of the camera 311 is mounted in a fixed position relative to the laser 313 but unlike the first aspect shown in FIG. 2, the camera 311 is slightly offset from the longitudinal axis of the laser 313. The camera 311 thus moves with the laser 313 towards and away along the longitudinal axis of the scanned socket 316. The scanned object, a prosthetic socket 316, is kept in place by a fixing base 317, which does not move so that the prosthetic socket 316 remains stationary during scanning. A physical origin coordinate 312, identified by a circled cross ⊕ and virtually placed or actually drawn on the surface of the prosthetic socket 316 provides a spatial reference point which will be useful to orient and align the physical prosthetic socket 316 with the virtual 3D model of the prosthetic socket 316 and with the 3D model of the bio-data.

In use, the laser 313 and the camera 311 move together to scan and map the interior surface of socket 316. The optical element 315 diffracts the laser light so as to produce a projected laser cone 301 on the surface of the scanned socket 316, where the laser cone 301 is projected, whereupon the process previously described of line acquisition, segmentation, calibration, distance-to-reference point calculation and line coordinates calculation is performed. These data are stored in a computer (not shown) and the motor 307 moves to the next incremental position, thereby moving the devices support frame 310 one unit of movement (typically but not limiting of the invention, 5 mm), and the entire process is repeated again until the entire socket 316 surface is scanned and mapped. At the conclusion of the process the data corresponding to each slice of socket surface is joined and a full 3D map of the lines is formed, thus rendering a virtual image of the socket 316 as shown in FIG. 1F.

Unlike the first aspect shown in FIG. 2, the second aspect of FIG. 3A does not have obstacles on the path of the camera 311 or the projected laser line 301, and there are therefore substantially no hidden areas on the socket 316 surface. It should be noted that data from any hidden areas can be reconstructed mathematically.

Figure 3B:
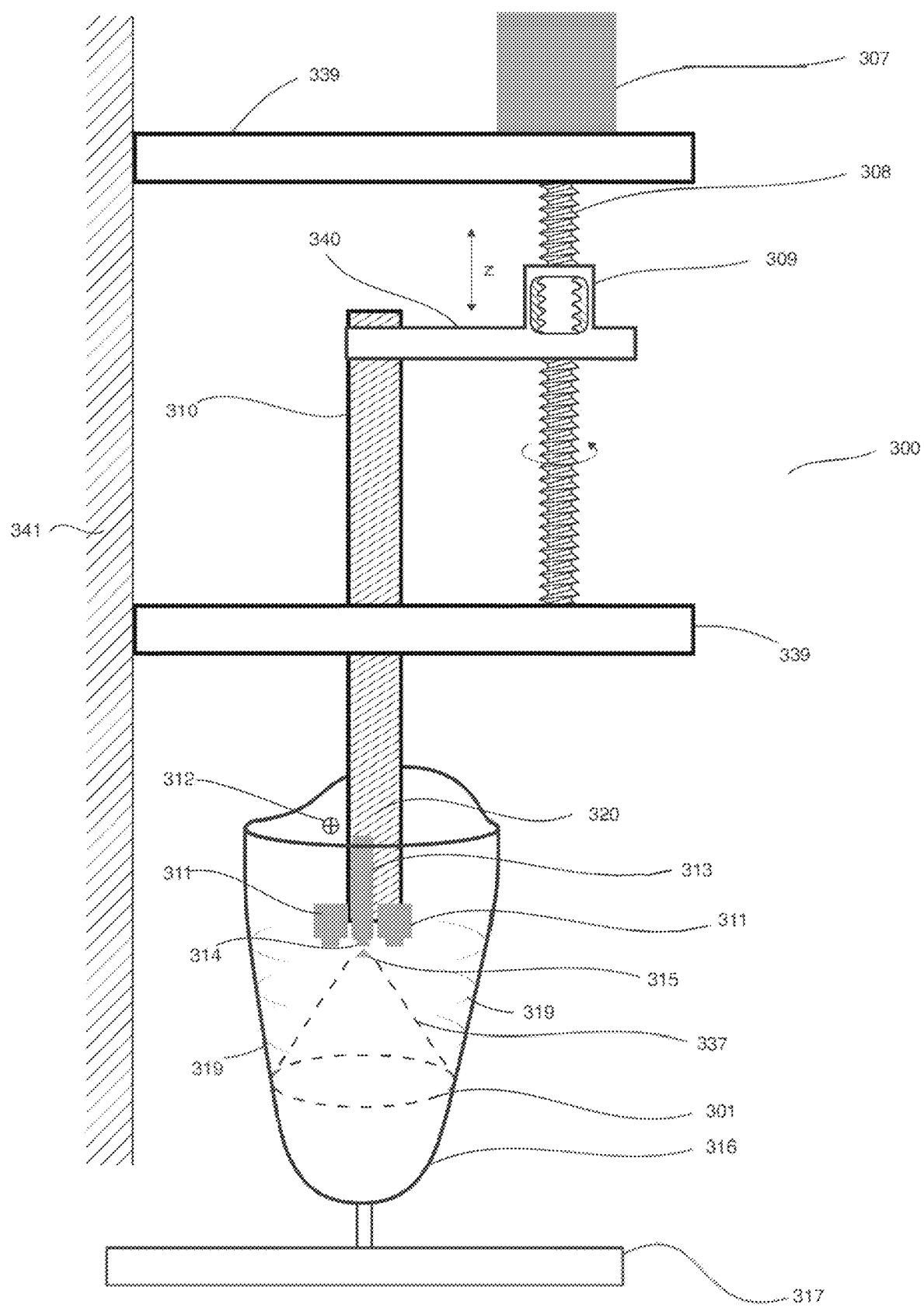
FIG. 3B is a section view of a third aspect of the laser and camera system.

A third aspect of the invention is shown in FIG. 3B which shows an arrangement with two (or more) cameras 311 positioned to the right and left of the laser 313. The other elements depicted in FIG. 3B are otherwise identical with those of FIG. 3A. The arrangement shown in FIG. 3B is able to scan more accurately the surface because more information from the two cameras 311 is gained and a stereographic picture can be formed.

In FIG. 4, there is shown a schematic representation of the first aspect of the invention, comprising a camera 411, a field of view 418 and a laser plane 401, created by the reflection of the laser beam from the laser 413 on the conic mirror 415. The camera field of view 418 has a centre C1, a length C3 and a width C2, so that the image which will be captured will have C3×C2 pixels and this number of captured pixels will vary depending on camera resolution of the camera 411. The laser plane 401 will have a variable shape depending on the surface and shape of the scanned object, e.g. the prosthesis socket 216 shown in FIG. 2. When scanning the socket 216, the laser plane 401 will project a circle of laser light with a centre L1 of a shape which will most frequently be roughly elliptical. L3 and L4 are examples of the variable diameters of that elliptical shape. In this first aspect, the centre points C1 and L1 are in the same x, y, and z position and will be considered to the reference point in this first aspect. By keeping a fixed distance L2 between the camera 411 and the laser plane 401, it is possible to determine a calibration rule that relates the dimension in pixels in the virtual image to the dimension in millimetres of the real scanned object (e.g. socket 216) and with this rule calculate the position of each point of the scanned object surface. By joining all these points acquired at each acquisition stage, a full model of the scanned object may be obtained.

Figure 5A:
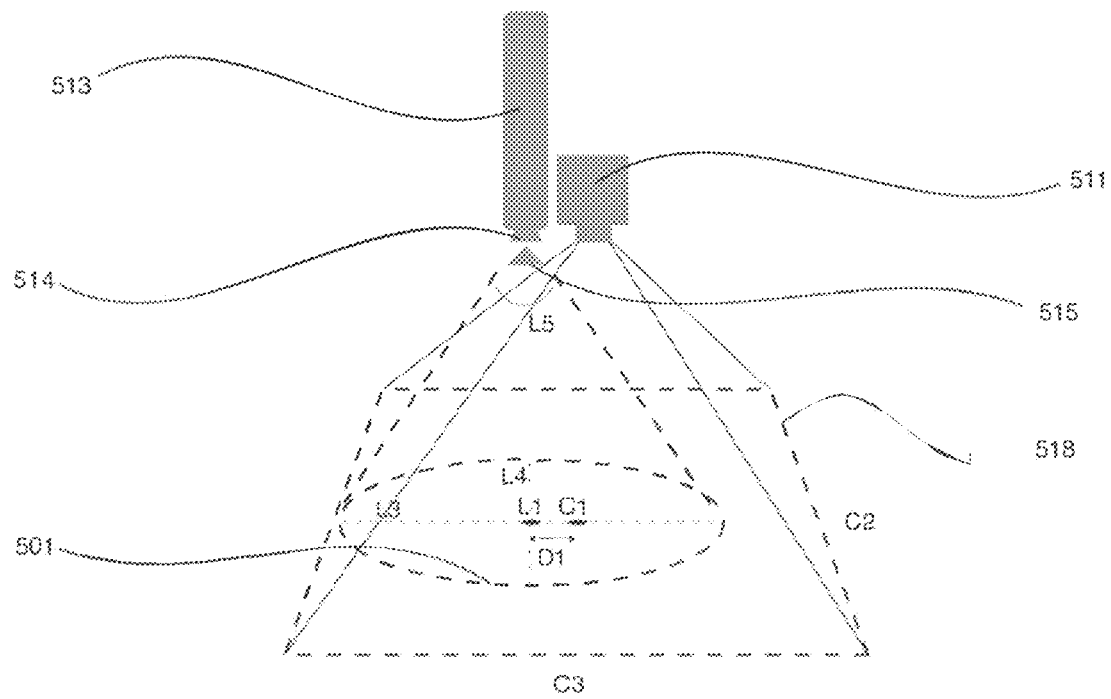
FIG. 5A is a representation of the laser plane and the camera field of view of the second aspect.
Figure 5B:
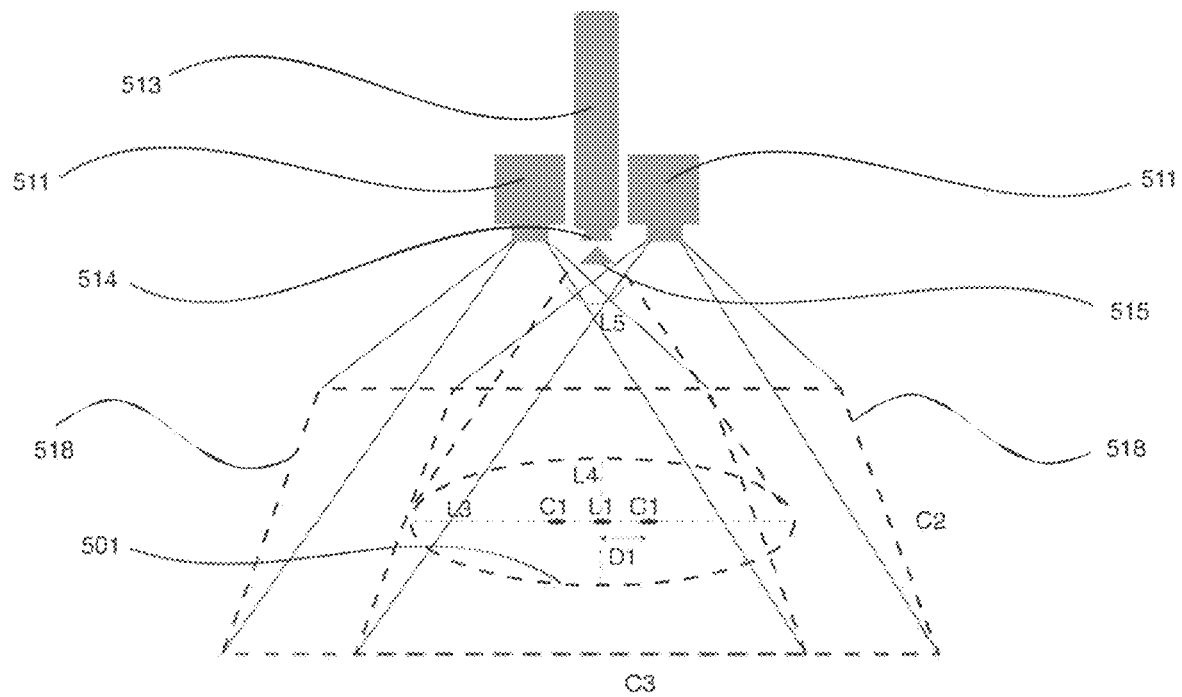
FIG. 5B is a representation of the laser plane and the camera field of view of the third aspect.

In FIGS. 5A and 5B, there are shown a schematic representation of the second aspect and the third aspect of the invention. These FIGS. 5A and 5B show a laser 513, a single camera 511 in FIG. 5A and two cameras 55 in FIG. 5B, a diffractive optical element 515, a single camera field of view 518 in FIG. 5A and two camera fields of view 518 in FIG. 5B and a projected laser beam 501. The projected laser beam 501 produces a pattern of know dimensions and shape. It could be for example, a cone or a grid pattern, but this is not limiting of the invention. It will be noted that the laser 513 and the camera(s) 511 are fixed in relation to each other. The diffractive element 515 creates a laser plane 501 with an angular opening L5. The laser plane 501 has a variable shape according to the scanned object shape and surface and the diffractive element 515. The camera field of view 518 depicted in FIG. 5A has a reference axis C1, a length C3 and a width C2. The projected laser beam produces a series of laser scans 501 along the reference axis will have a variable shape depending on the surface and shape of the scanned object. When scanning the socket 316 of FIG. 3, each successive laser scan 501 be imaged as a two-dimensional image in the camera(s) 511 will again have a reference point L1 on the reference axis and L3 and L4 are examples of the points of the scan.

However, in this second aspect shown in FIG. 5A, camera field of view reference point C1 and laser reference point L1 are in different positions and the distance D1 between the camera field of view reference point C1 and the laser plane reference point L1 is a function of the distance between the reference axis of the laser 513 and the reference axis of the camera 511. The field of view reference point C1 will always be on the same longitudinally oriented reference axis of the camera in successive ones of the (two-dimensional) images taken at each of the image acquisition stage. However, the laser plane reference point L1 in the camera field of view will vary as the surface of the scanned object 316 approaches the camera 511 or moves away from the camera 511. For a given point of the projection of the laser beam on the scanned object 316, it is possible to define a line of view from the point of projection to the camera(s) 511. The world coordinates of this given point will be the intersection of this line of view from the camera(s) 511 to the projected laser pattern. These variable distances and the changing of the laser reference point L1 require appropriate calculation, calibration and dynamic calibration methods, to relate the virtual dimensions of each of the series of images acquired by the camera 511 with the real dimensions in millimetres of the scanned object surface upon which the projected laser beam 501 is projected and thus to determine with precision the correct coordinates of each point of the projected laser beam 501 and therefore the correct surface measurement of the scanned object 316. This variable value of distance D1 only occurs in the images (virtual D1). In reality, the distance between the reference axis of the laser 513 and the reference axis of the camera 511 (real D1) is always substantially the same, thus allowing to compute the dynamic calibration method.

Similar issues occur with the third aspect of the invention shown in FIG. 3B, which includes two cameras 311. The third aspect is different from the second aspect in the sense that the two (or indeed more) cameras 311 require a variation of the method for achieving the 3D reconstruction. As described with respect to the first and second aspects, the cameras 311 and laser 313 are moved along the vertical axis and the projected laser beam 337 is captured by both of the cameras 311. This capture can be simultaneously performed or statically.

The relative orientation/position and origin of the field of views of the cameras 311 is known and thus by identifying a given physical reference (i.e. a point 301 of the projected laser beam) in the captured image by both cameras 311, it is possible to infer the relative position of the point 301 of the projected laser beam 337 to the reference axis. The reference axis has an origin between the cameras 311. This same physical reference of the point 301 captured by both of the cameras 311 is represent by different pairs of pixels in the two-dimensional images taken by the cameras 311 and it is this difference combined with the position and orientation between cameras 311 that enables the calculation of the three-dimensional position of the points 310 on the projected laser beam 337.

To find the relative position between both of the cameras 311 (after being placed in the camera mount), several images of a given reference figure should be captured simultaneously by both cameras 311, at different distances and orientation to the cameras 311. For example, the given reference figure could be a chessboard, but this is not limiting of the invention. By identifying key-points in this reference figure in both of the captured images (either by manually picking or automatic processing) and previously knowing their real/physical distances between key points in the reference figure, it is possible to mathematically determine the relative position between the field of view of both of the cameras 311.

Both the sockets 316 in FIGS. 3A and 3B have bio-sensors 319 as explained in connection with FIG. 2. A light source 320 illuminates the bio-sensors 319 and the camera(s) 311 record the position of the bio-sensors 319. In the case of FIG. 3B, there are two light sources 320.

Figure 6:
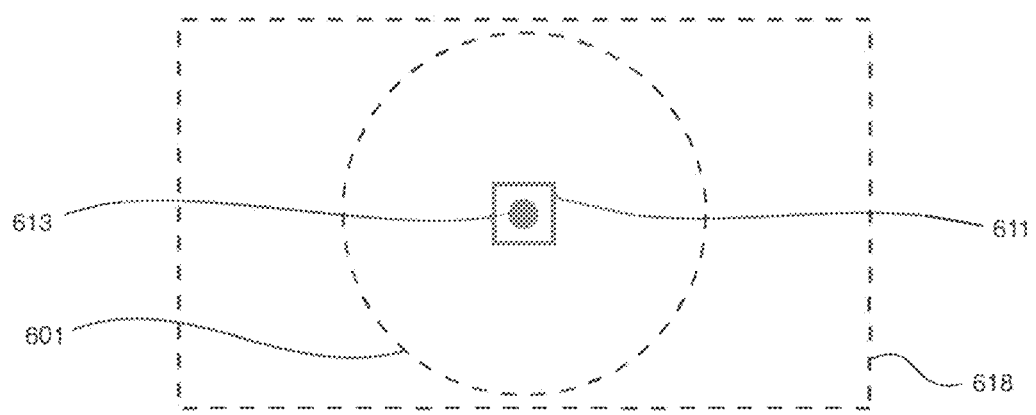
FIG. 6 is a top view of the laser plane and the camera field of view of the first aspect.

FIG. 6 illustrates a top view of the first aspect, comprising the camera 611 and the laser 613, and their respective longitudinal axes are aligned along the same axis. The laser plane 601 is centred and inside the camera field of view 618.

Figure 7A:
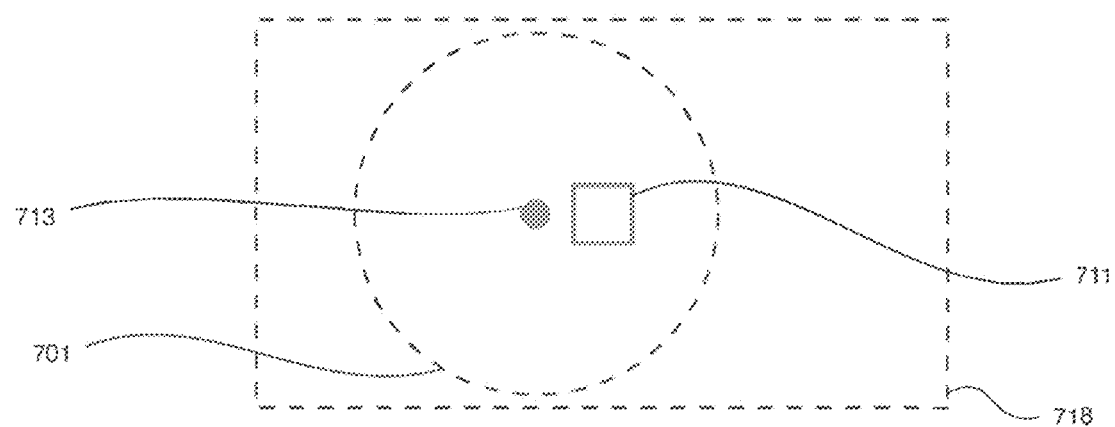
FIG. 7A is a top view of the laser plane and the camera field of view of the second aspect.
Figure 7B:
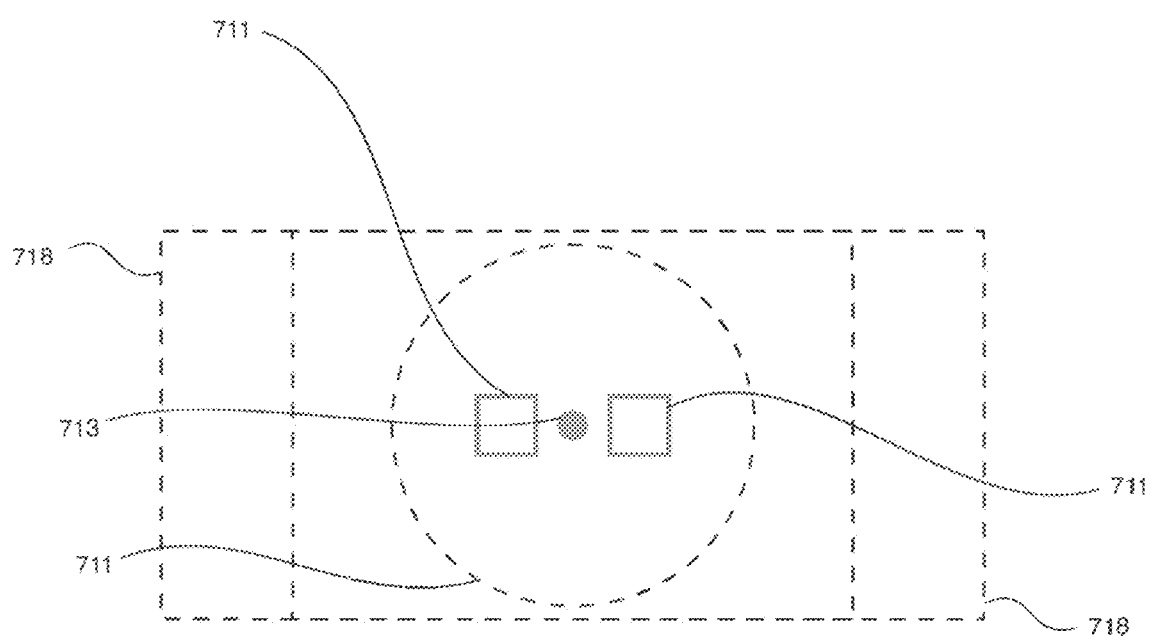
FIG. 7B is a top view of the laser plane and the camera field of view of the third aspect.

FIG. 7A shows a top view of the camera 711 and the laser 713 in the second aspect, showing the two devices, the camera 711 and the laser 713 to be placed no longer along the same axis, but offset from each other, resulting in the centre of laser plane 701 to be different from the reference axis, i.e. centre of camera field of view 718. Similarly, FIG. 5B shows the same top view of the third aspect of the invention with two cameras 711.

It will be appreciated that the use of the two cameras 311, 511, 711 in the third aspect of the invention means that both cameras 311, 511, 711 need to be calibrated in order to know the precise relative position and pose between the two cameras 311, 511, 711 and the lens distortion in each of the two cameras. These parameters are always different due to manufacturing variability.

To calibrate the cameras 311, 511, 711 and to compensate for difference in the lens parameters of the cameras 311, 511 and 711, a method based on Zhang. "A Flexible New Technique for Camera Calibration" published in IEEE Transactions on Pattern Analysis and Machine Intelligence, 22(11):1330-1334, 2000, is used. This method requires a custom-designed camera mount which holds both cameras 311, 511, 711 and the laser 313, 513, 713 i.e. the same laser that will be used in the laser scanner system. In the calibration, a chessboard design placed in a flat surface is used as a reference figure. The dimensions of the squares of the chessboard is known. A number of pictures are taken simultaneously from both of the cameras 311, 511, 711 in which the chessboard is placed at different distances to the cameras 311, 511, 711 and at different orientations.

The corners of the chessboard of every pair of images taken from the cameras 311, 511, 711 are detected. The number of squares of the chessboard are known and thus it is simple to match the corners detected by both of the stereo images taken from the two cameras 311, 511, 711. The chessboard plane is considered to be at z=0, only leaving the problem to be solved only in this plane (with origin in one of the corners of the chessboard).

Each of the images is automatically processed in order to find the chessboard patterns, acquiring one conversion from the image corner pixels to the real 3D positions of the chessboard. This enables the computation of the intrinsic lens parameters for each of the cameras 311, 511, 711 (i.e. distortion coefficients), by trying to minimize the 2D<->3D re-projection error in all images. After carrying out this calculation, it is possible to use these 2D-3D correspondences to calculate the transformation matrix between the images from the two cameras 311, 511, 711.

This calibration enables the computation of the matrix which projects the images of both cameras 311, 511, 711 onto a common image plane, i.e., to rectify the images. This process makes it easier to find correspondences between the stereo images because the process aligns the image in such a way that theoretically it is only necessary to search along a single line (if the calibration is accurate, correspondent points are in the same row of the rectified images). After constructing the undistorted and coplanar image planes, the 3D reconstruction can be achieved by triangulation.

Figure 8A:
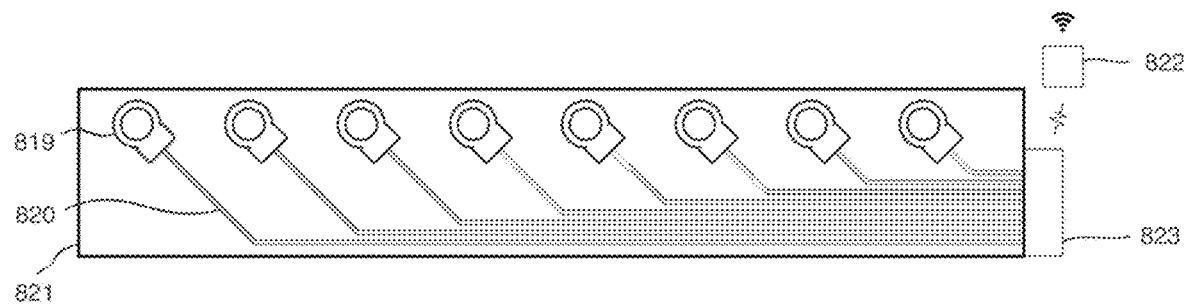
FIGS. 8A, 8B and 8C are representations of the bio-sensors strip

FIG. 8 now illustrate the bio-sensors. FIG. 8A shows a top view of bio-sensor strip 821 comprising bio-sensors 819 and power and data leads 820, which in turn connect to a power and data connector 823, itself connected to a transmitting device 822 that can be connected, preferably wirelessly, to a computer or handheld mobile smart device (not shown).

Figure 8B:
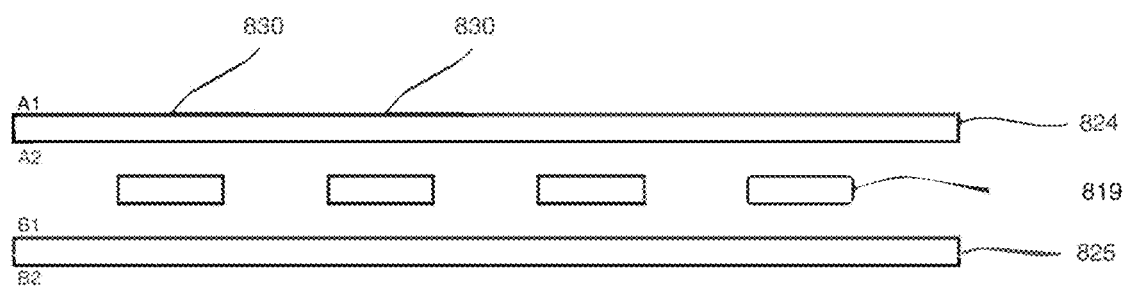

FIG. 8B shows a section view of the bio-sensor strip of FIG. 8a, comprising two strips of plastic film 824 and 825, which sandwich the bio-sensors 819. In one aspect, the bio-sensor 819 are pressure sensors, but as noted elsewhere, other types of sensors can be used. The bio-sensor comprises a pressure-sensitive resistor which resistance changes depending on the load or pressure applied to the bio-sensor 819. Measurement of the change of resistance is carried out using a bridge circuit.

The power leads and data leads 820 made, for example, of silver ink are not illustrated in this FIG. 8B. Side A1 of plastic film 824 will be in contact with the stump skin, i.e. the skin on the residual limb, or the liner covering the residual limb, and will preferably have a bio-compatible finish. A non-limiting example of the bio-compatible finish is polyurethane. Side A2 of the plastic film 824 faces the bio-sensors 819 and holds the bio-sensors 819 in place. Preferably, the side A2 has an adhesive finish from, for example, a medical grade acrylic adhesive, so that the bio-sensors 819 do not move.

Side B1 of polymer film 825 on FIG. 8B faces the bio-sensors 819 and holds the bio-sensors 819 in place. The side B1 may have an adhesive finish, e.g. from a medical grade acrylic adhesive, so that bio-sensors 819 do not move. The side B2 of the plastic film 825 is, for example, silicone and will be in contact with the prosthetic socket surface of the prosthetic surface 216, 316 (not shown in FIG. 8B). The side B2 will preferably have an adhesive finish, so that the bio-sensor strip 819 is firmly held in place on the socket surface.

The side A1 of the plastic film 824 will have one or more markings 830 on the surface. These markings are illuminated by the light source 220, 320 to locate the bio-sensors on the inside of the socket 216, 316 as explained previously. In one non-limiting aspect, the markings are multi-coloured roundels (concentric circles). The different colours are used to indicate differing positions or the different types of bio-sensors within the socket 216, 316. Currently, at least two markings per strip are required to uniquely identify the position of the bio-sensor strip 819, but a single marking could be acceptable.

Figure 8C:
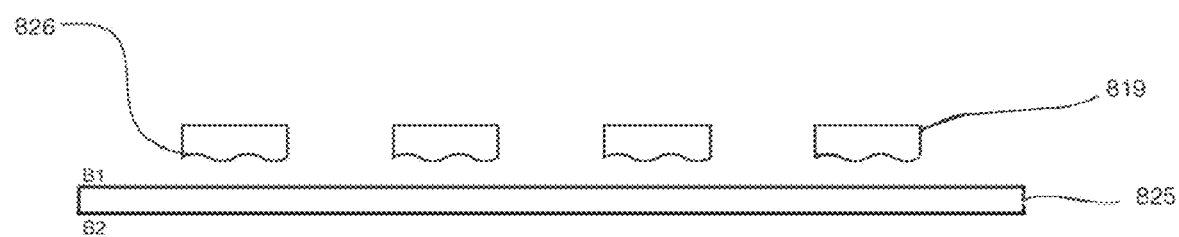

FIG. 8C shows a section view of a simpler embodiment of the bio-sensor strip 819, comprising a single plastic film 825, to which the bio-sensors 819 with an adhesive finish 826 are applied to the B1 side of the plastic film 825. This side B1 faces the stump skin and has a bio-compatible finish, while side B2 of plastic film 825 will be in contact with the prosthetic socket surface of the prosthetic socket 216, 316 and will preferably have an adhesive finish, so that the bio-sensor strip 819 is firmly held in place on the socket surface. It will be appreciated that the sides B1 and B2 could be reversed so that B2 is in contact with the stump skin.

Before use, the bio-sensor strips 819 are covered on the adhesive side with a peelable cover if dispensed in pre-cut strips, or not covered if they are dispensed in rolls. In use, the peelable covers are removed, the bio-sensor strips 820 are cut to the right size, if needed, and the bio-sensor strips 820 are applied to the internal surface of the prosthetic socket 216, 316, in the orientation best determined by the prosthetic fitting technician's experience.

The biosensor strips 819 can measure different types of biodata, which include but are not limit to pressure between the stump skin and the prosthetic socket surface, or temperature. In one non-limiting example, the biosensor strips are formed of a force sensing resistor comprising at least one polymer layer whose resistance varies on application of a pressure. The change in the resistance can be measured, for example, by a bridge circuit. In one aspect of the bio-sensor a plurality of polymer layers is used with different characteristics to allow a wide range of different pressures to be measured.

Figure 9:
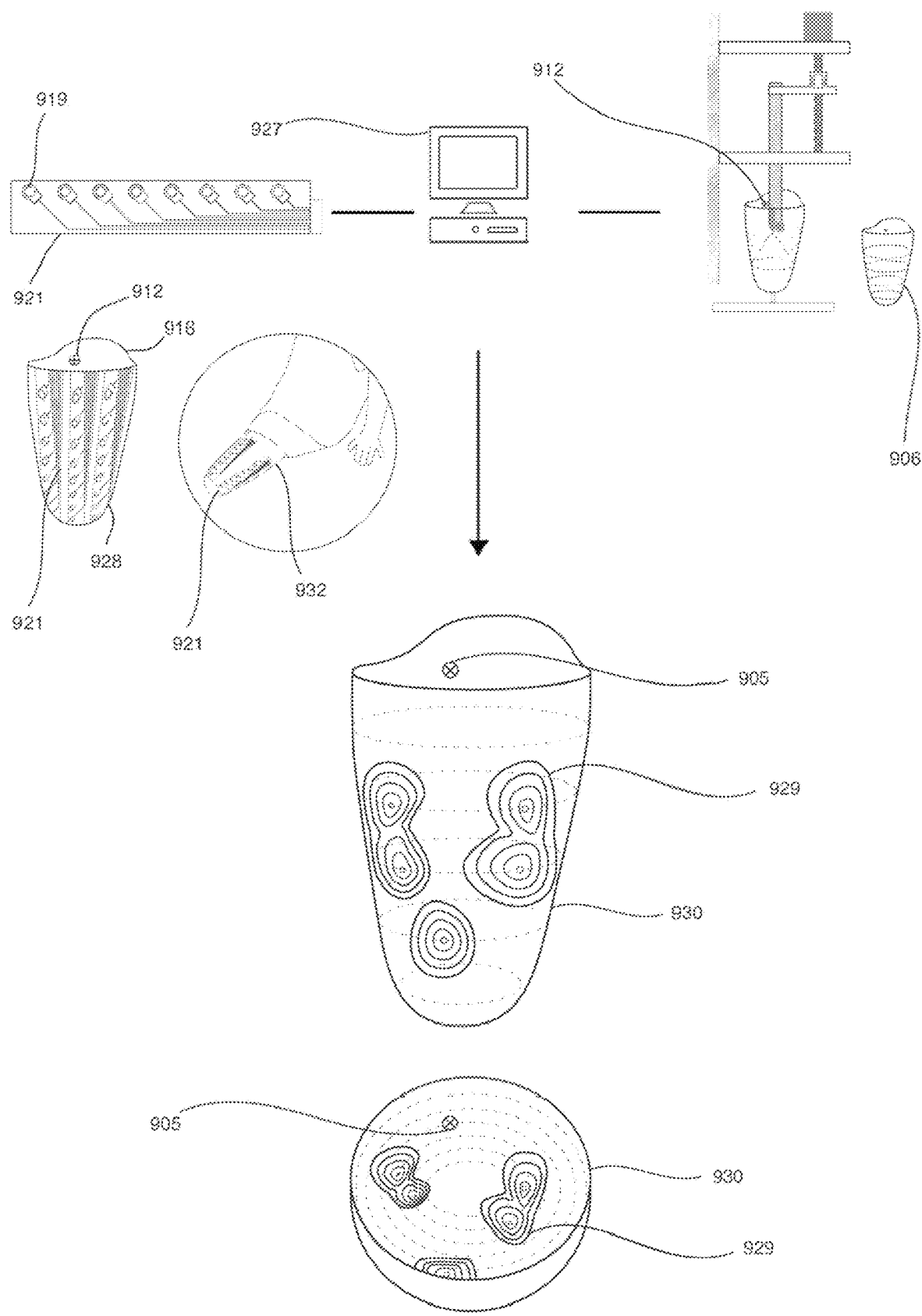
FIG. 9 is a conceptual representation of the invention combining the bio-sensor data with the socket surface map, resulting in a superimposed bio-data and virtual socket surface map.

FIG. 9 shows the elements of the complete system of the present invention. The bio-sensor strip 921 comprising the bio-sensors 919 acquires the bio-data which is transmitted to a computer, a hand-held device or similar data processing device 927. The bio-sensor strips 921 are applied to an internal surface of the prosthetic socket 916, resulting in a sensorized socket 928, which will receive a residual stump 932 of the residual limb. The bio-sensor strips 921 are positioned in relation to the real origin coordinate 912, which is known or which can be automatically determined by the light source 220, 320 scanning system as shown and described with respect to FIGS. 2 and 3. The data from each of the bio-sensors 919 can be overlaid on the socket surface map 906 generated by the light source scanning system by using a computing device 927, resulting in a 3D bio-data profile 930. The 3D bio-data profile 930 can be oriented by relating the virtual origin coordinate 905 with the real origin coordinate 912, allowing the accurate representation of the bio-data profile 929 with the socket surface map 906.

Furthermore, the spacing between the bio-sensor strips 921 can be adjusted to vary the resolution of the data obtained—the bio-sensor strips 921 can be arranged closer together or even on top of each other with an offset in areas where greater data resolution is required. When evaluating pressure, a correct fit between the stump 932 and the socket 916 will produce uniform pressure distribution across certain areas of the surface of the socket 916, depending on the socket type, while a poor fit will produce areas of altered pressure which will be evidenced by more concentrated curves in the bio-data profile 929, in zones where this should not occur.

It will be appreciated that absolute values from the bio-sensors are not required. The values can be normalised or otherwise mathematically manipulated with respect to the maximum value recorded.

Artificial colour may be added to the bio-data profile 929 to create a heat map and thus illustrate the areas of pressure. Shifts in the colour may be used to differentiate between areas of equally uncomfortable areas of increased or reduced pressure, such as red for higher pressure, and blue for lower pressure. The prosthesis technician can therefore identify high pressure areas of the socket 916 which need fine tuning and shaping back as well as areas of lower pressure which indicate regions of the socket 916 which need building up. Other types of bio-data of interest may be represented using the same method.

The arrangement of the bio-sensors 919 on the bio-sensor strips 921 enables the system to be wearable, non-invasive, autonomous (with long battery time), modular, flexible (with different placement of sensors), scalable (more sensors as needed), and versatile (different type of modules/sensors).

The images of the bio-sensor strips 921 are drawn on the surface of the stump 932 to indicate their location in relation to the stump 932. The real origin coordinates 912 are actually or virtually drawn on the scanned socket 916 and the scanning and data acquisition apparatus produces the 3D image of the scanned socket 906.

An example can serve to illustrate this in more detail. Suppose the prosthesis is an artificial leg or an artificial arm. In use, the patient with the artificial leg is made to walk (in the case of a leg) or move (in case of an artificial arm) for a certain amount of time until sufficient bio-sensor data has been obtained from the bio-sensors 919 to produce the virtual 3D bio-data profile 930 comprising bio-data profile curves 929 of the pressure, temperature or any other bio-data of interest. The position of these bio-data profile curves 929 is known by reference to virtual origin coordinates 905 of the 3D bio-data profile 930.

It is also possible to combine the bio-sensor data with data from one of more inertial motion units which is carried by the patient and attached to the limb. The inertial motion unit will have three, six or nine axes and provide information about the changes in the data as the patient moves. This data can be used to characterise potential gait anomalies.

Figure 10A:
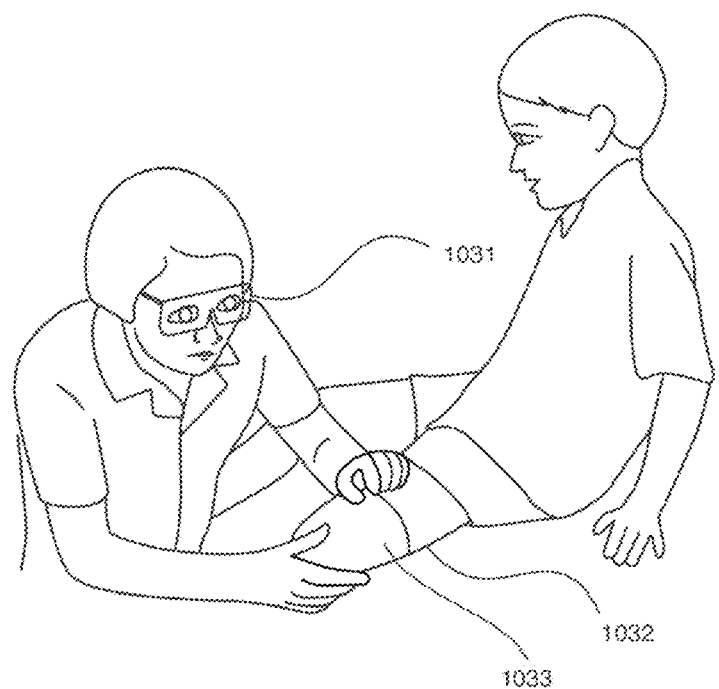
FIGS. 10A to 10F describe the invention in use, showing a prosthetic technician and a patient with an amputated leg, where the technician is using virtual reality vision system to better observe areas to adjust in the socket.
Figure 10B:
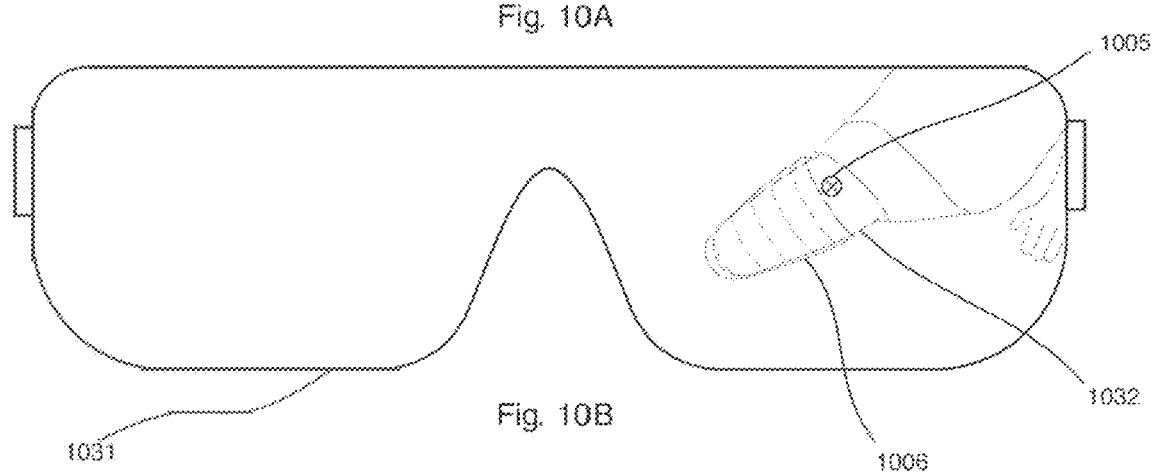
Figure 10C:
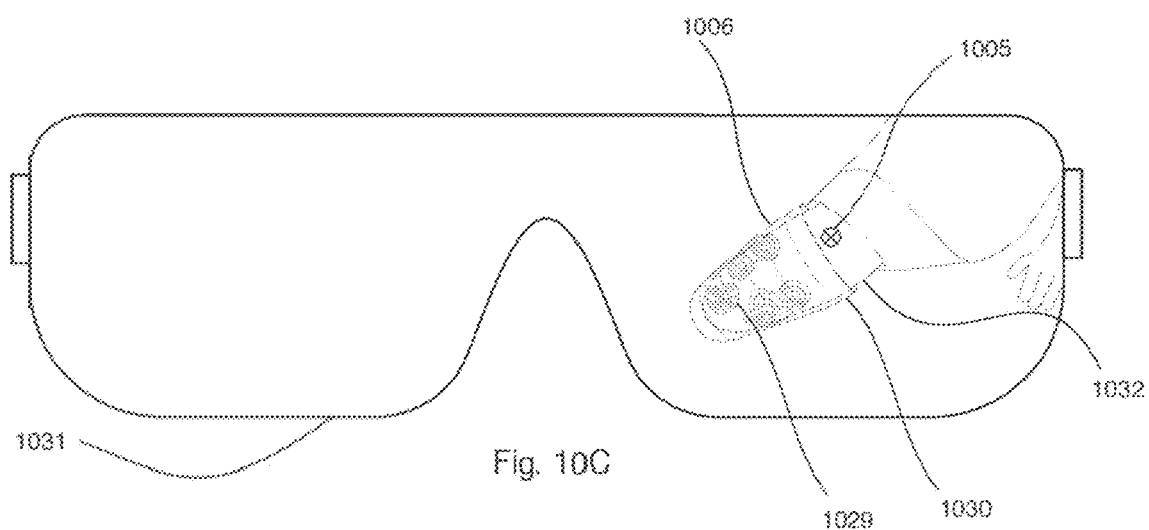

FIGS. 10A-C shows the fitting of a prosthetic leg using the components of the present invention, using a virtual reality or augmented reality vision system.

FIG. 10A shows a prosthesis fitting technician using a virtual reality or augmented reality vision system 1031 and the residual member 1032 of a user. It will be noted that some residual members 1032 are covered with liners or socks, part of which is shown as 1033 on the figure.

FIG. 10B shows what the prosthesis fitting technician sees through the virtual reality or augmented reality vision system 1031, which superimposes the 3D surface map 1006 of the socket 916, which has been obtained by the scanning, imaging and surface determination system of the present invention, with the virtual origin coordinate point 1005 of the socket 916, themselves precisely aligned with the user's residual limb 1032, in the same limb location where the socket 916 was worn during the testing and data acquisition phase (walking, moving). This allows the prosthesis fitting technician to correctly identify the problematic areas of the socket 916.

Furthermore, a light grid may be projected onto the patient's stump or over the surface of the actual socket 916 which is calibrated to the 3D socket model so as to help the prosthetic fitting technician to correlate the 3D image with the actual socket surface of the socket 916 and hence help identify the areas that need adjustment on the actual socket surface.

FIG. 10C shows the same image as FIG. 10B, but now the virtual reality or augmented reality vision system 1031 of the present disclosure adds the layer of the bio-data profile 1030 and the bio-data profile maps 1029 to FIG. 10B. At the virtual origin coordinate point 1005 two virtual origin coordinate points are precisely superimposed: the origin point of the 3D socket surface map 1006 and the origin point of the bio-data profile 1030, both precisely aligned with the same limb location where the socket 916 was worn during testing. The alignment of all of these origin coordinate points is needed so that bio-data obtained actually matches the appropriate area of the physical socket 916 and the corresponding area of the residual limb 1032 location.

The purpose of the layering of the various data maps is to evidence the areas where pressure, temperature or other data are more intense, and which may indicate areas of pain or discomfort for the person wearing the prosthesis, or less intense which may indicate areas which lack support.

Figure 10D:
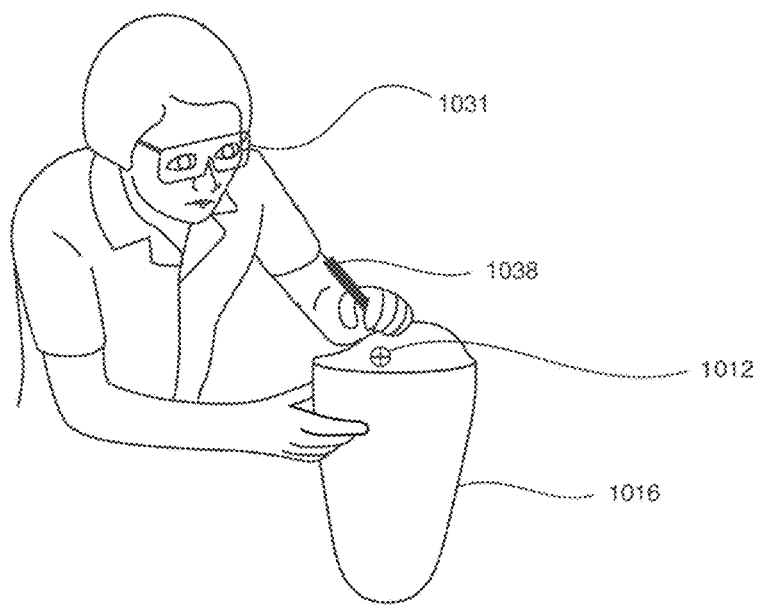

In FIG. 10D, the prosthetic fitting technician is now shown holding the socket 1016 and a shaping tool 1038. The prosthetic fitting technician will now begin to shape the socket 1016, using the virtual reality or augmented reality vision system 1031, which is able to correctly display all of the data obtained by the virtual reality vision system 1031 and to referencing the data to the physical socket 1016 by identifying the real origin coordinate point 1012 on the socket 1016.

Figure 10E:
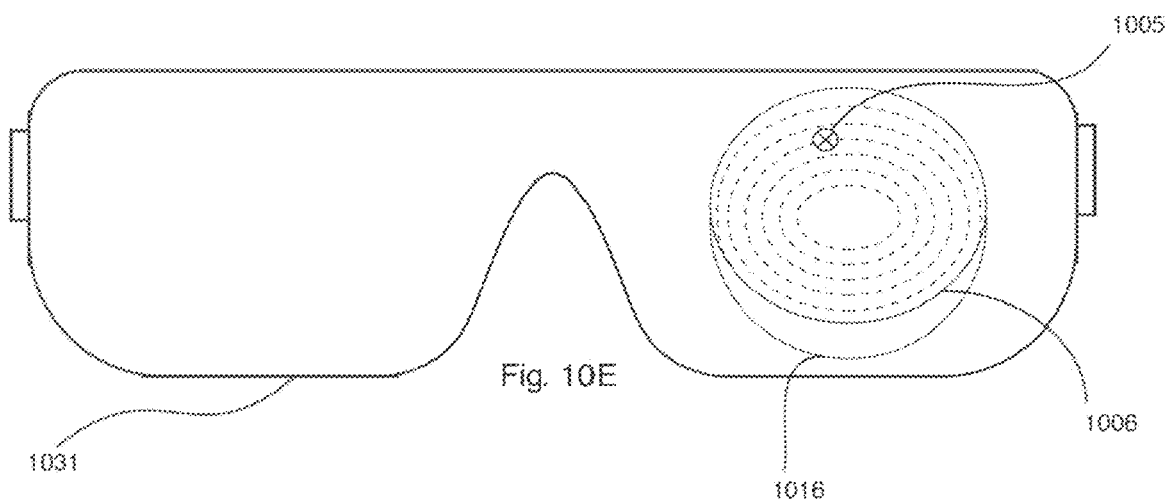

FIG. 10E shows the visualization of the 3D socket surface map 1006 over the actual prosthetic socket 1016, using the virtual reality or augmented reality vision system 1031. This displays the information of the 3D socket surface map 1006 over the corresponding zones of the prosthetic socket 1016, which can be achieved by using the virtual origin coordinate 1005.

Figure 10F:
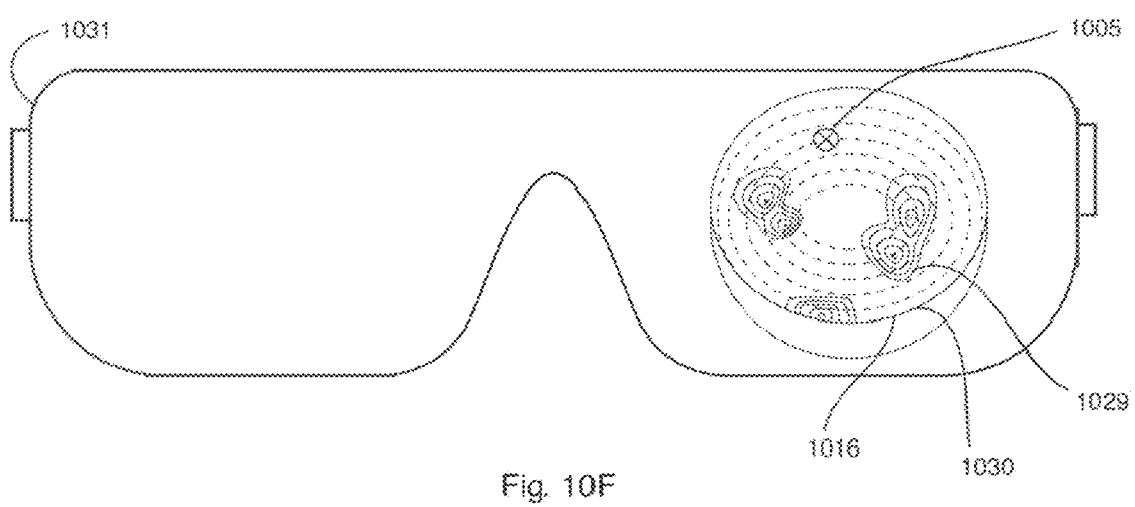

FIG. 10F shows the visualization of the 3D bio-data profile 1030 over the physical prosthetic socket 1016, using the virtual reality vision system 1031. The display of the information of the 3D bio-data profile 1030 is overlaid onto the corresponding zones of the prosthetic socket 1016, which can be achieved using the virtual origin coordinate 1005 of three data sets (bio-data profile curves, socket surface model and physical stump) and overlapping the bio-data profile curves 1029 over the surface map 1006, allowing the prosthetics fitting technician to correctly and quickly identify the areas that require adjustment.

FIG. 11 shows a similar process to that described in FIGS. 10A-F, but now the prosthetics fitting technician is using an augmented reality device, such as a portable smart tablet equipped with augmented reality software and appropriate rendering and layering software. This avoids using the cumbersome virtual reality vision system and allows the technician to observe all of the necessary information on the same plane.

Figure 11A:
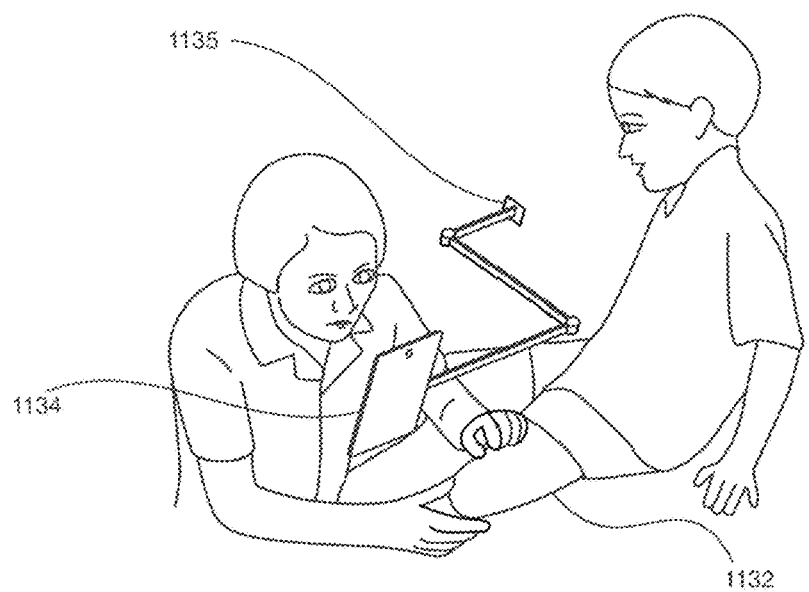
FIGS. 11A to 11F describe the invention in use, showing a prosthetic technician and a patient with an amputated leg, where the technician is using an augmented reality device to better observe areas to adjust in the socket.

In FIG. 11A shows the prosthetic fitting technician using a handheld device 1134, such as a tablet or any other mobile device, mounted on a flexible arm support 1135 fixed to a solid surface such as a wall or table (not shown) to examine the patient's residual limb 1132.

Figure 11B:
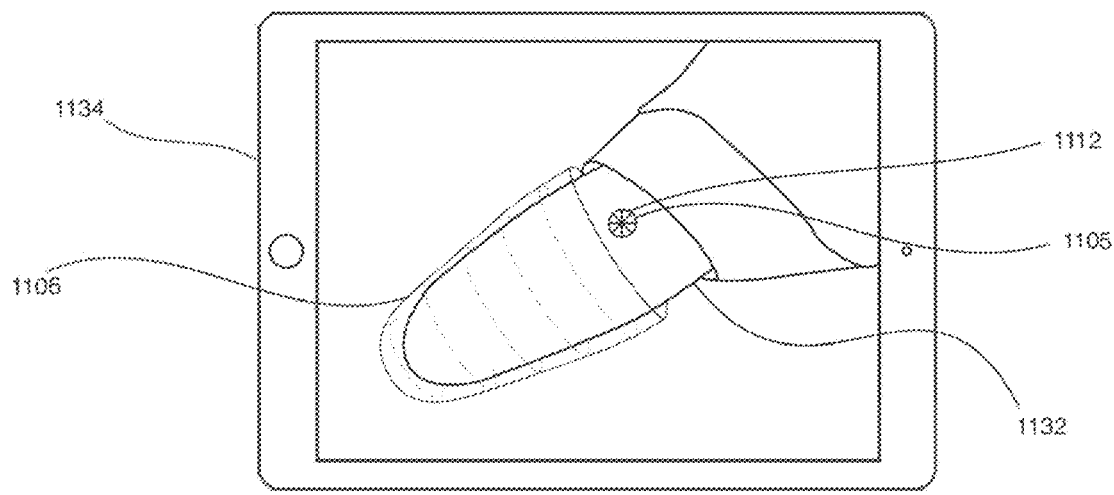

FIG. 11B shows the image as seen by the technician of the socket surface map 1106 superimposed over the amputee residual limb 1132, using the handheld device 1134. This handheld device 1134 displays the information of the socket surface map 1106 over the corresponding zones of the residual limb 1132. Both images are aligned by means of both the virtual socket origin coordinate 1105 and the real stump origin coordinate 1112.

Figure 11C:
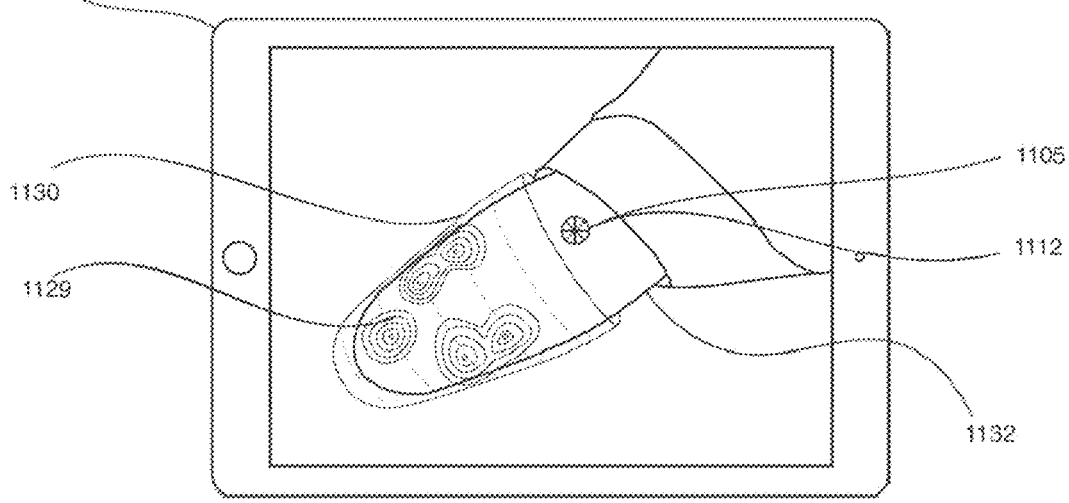

FIG. 11C now adds to the handheld device's display 1134 the visualization of the 3D bio-data profile 1130 over the amputee residual limb 1132, using the handheld device 1134. This displays the information of the 3D bio-data profile 1130 over the corresponding zones of the residual limb 1132, which can be achieved using both the virtual socket origin coordinate 1105 and the real stump origin coordinate 1112, and overlapping the bio-data profile curves 1129 over the socket surface map 1106, allowing the prosthetics fitting technician to correctly and easily identify the problematic areas and to shape the problematic areas.

Figure 11D:
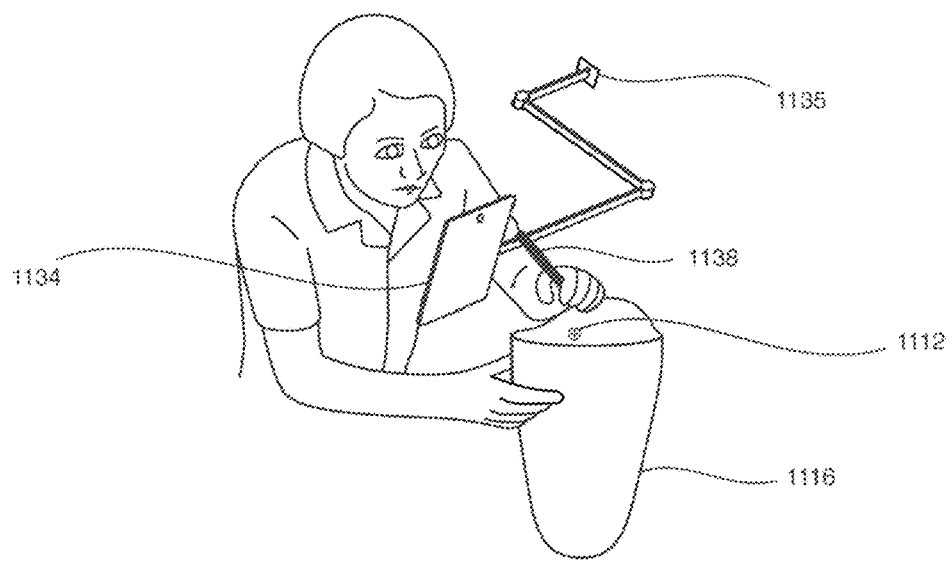

In FIG. 11D, the prosthetics fitting technician goes to work with a shaping tool 1138 on the socket 1116 which is observed by means of the handheld device 1134 mounted on a flexible arm support 1135 and which is oriented by means of the real origin coordinate 1112.

Figure 11E:
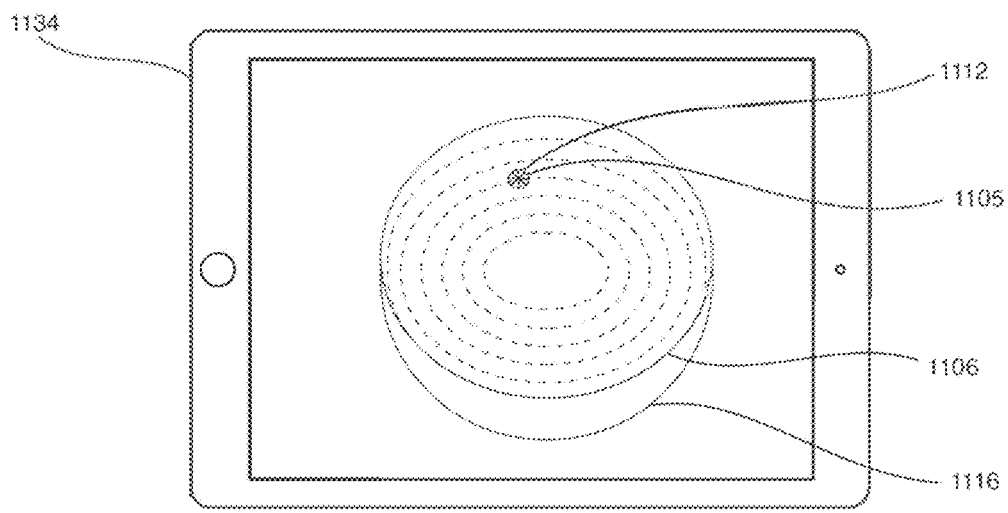

FIG. 11E shows the image as seen by the technician of the surface map 1106 over the prosthetic socket 1116, using the handheld device 1134. This handheld device 1134 displays the information of the surface map 1106 over the corresponding zones of the physical prosthetic socket 1116, which can be achieved using both the virtual origin coordinate 1105 and the real origin coordinate 1112.

Figure 11F:
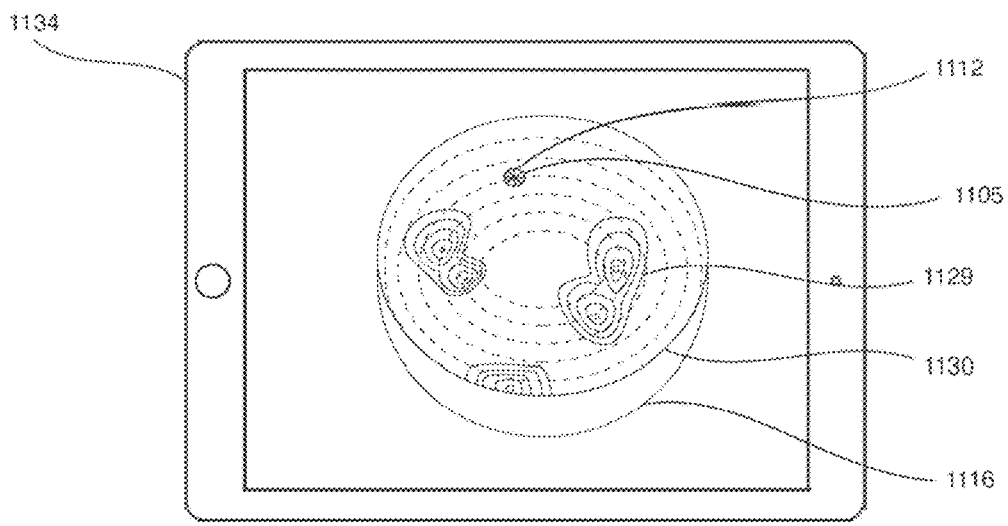

FIG. 11F now adds to the handheld device's display 1134 visualization of the 3D bio-data profile 1130 over the prosthetic socket 1116, using a handheld device 1134. This displays the information of the 3D bio-data profile 1130 over the corresponding zones of the prosthetic socket 1116, which can be achieved using both the virtual origin coordinate 1105 and the real origin coordinate 1112 and overlapping the data profile curves 1129 over the surface map 1106, allowing the prosthetics fitting technician to correctly and quickly identify the problematic areas.

The alignment of the socket surface map 1106 and/or the 3D bio-data profile 1130 over the object of interest can be achieved by using the same origin coordinate in the real object (real origin coordinate 1112), in the socket surface map 1106 (virtual origin coordinate 1105) and in the 3D bio-data profile 1130 (virtual origin coordinate 1105), or by resorting to a best match algorithm, that computes the best geometrical match between two 3-dimensional objects.

Figure 12:
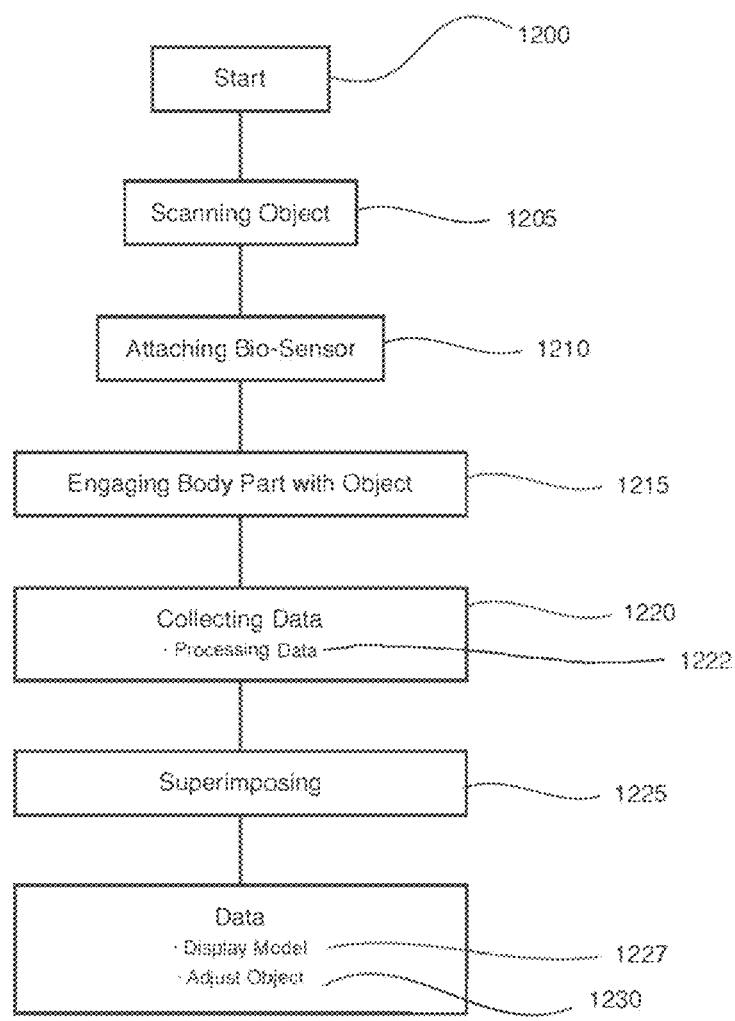
FIGS. 12 and 13 show flow diagrams of the method

The method will now be described with respect to the flow diagrams shown in FIGS. 12 and 13. The method starts at step 1200 and the object 216, 316, for example the prosthesis 932, is scanned in step 1205. A plurality of the biosensors 919 are attached to either the surface of the object 216, 316 or the body part, for example the stump 919, in step 1210. The object 216, 316 is subsequently engaged with the body part 919 in step 1215 and data is collected in step 1220 from the bio sensors 919. The collected data is processed in step 1222 and superimposed in step 1225 over the surface map 1006 of the object 216, 316 to identified areas of the object 216, 316 that need to be adjusted. The superimposed data on the surface map 1006 is displayed as a 3D model to the user, for example the prosthetics fitting technician, in step 1227 before adjustments are made in step 1230.

Figure 13:
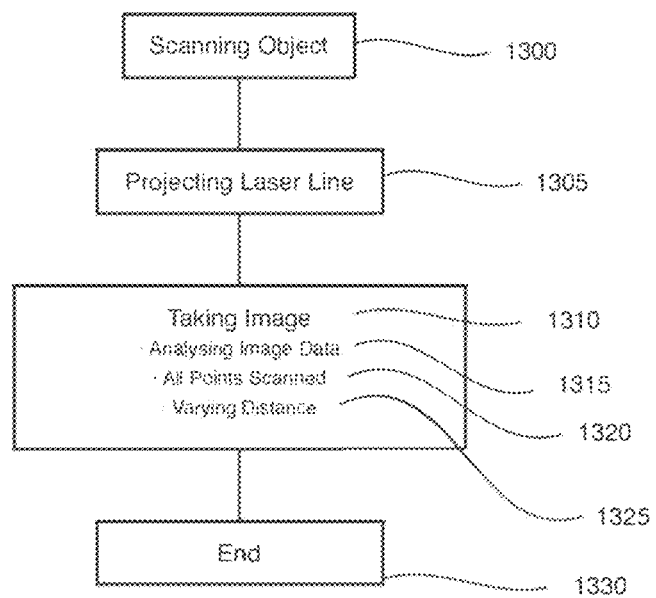

The method for creating the surface map is shown in FIG. 13 which starts with scanning the object 216, 316 in step 1300 using a laser 213, 313 projecting a laser line 201, 301 on the surface of the object 216, 316. An image of the object 216, 316 with the laser line 201, 301 is taken in step 1310 and the image data analyses in step 1315. If all of the object 216, 316 has been scanned in step 1320, then the method is completed in step 1330 and the surface map of the object 216, 316 is created. Alternatively, the distance between the laser and the object 216, 316 is moved to scan a different part of the object 216, 316 in step 1325.

The present invention comprising the use of the biosensors, the mapping of the internal surface of the prosthetic socket, the generation of bio-data related to socket/stump fit and the identification of socket areas which require adjustment represents several economic and comfort benefits. The method is non-invasive, unobtrusive and does not require a clinician's attendance. It saves considerable time in the fitting process, thereby reducing cost and increasing the patient's quality of life.

REFERENCE NUMERALS

101 Laser Line
102 Centre
103 Data Points
104 Laser line
105 Origin coordinates
106 Surface map
200 Conical laser assembly
201 Projected radiation line
207 Motor 208 Linear screw
209 Bushing
210 Support frame
211 Camera
212 Physical origin coordinate
213 Laser
214 Laser lens
215 Conical mirror
216 Socket
217 Fixing base
219 Bio-Sensors
220 Radiation source
236 Radiation beam
239 Anchor frame
240 Support assembly
241 Wall or housing
300 Conical laser assembly
301 Projected radiation pattern
307 Motor
308 Linear screw
309 Bushing
310 Device supporting frame
311 Camera
312 Original coordinate
313 Laser
314 Laser lens
315 Optical element
316 Scanned socket
317 Fixing base
319 Bio-sensors
320 Radiation source
339 Anchor frame
340 Support Assembly
341 Wall or housing
401 Laser Plane
411 Camera
413 Laser
415 Conic mirror
418 Field of view
501 Laser plane
511 Camera
513 Laser
515 Optical Element
518 Field of view
601 Laser plane
611 Camera
613 Laser
618 Field of view
701 Laser plane
711 Camera
713 Laser
719 Field of view
819 Bio-sensors
820 Data Leads
821 Bio-sensor strip
822 Transmitting device
823 Power and data connector
824 Plastic film
825 Plastic film
826 Adhesive finish
830 Markings
905 Virtual original coordinates
906 Socket surface map
912 Real origin coordinate
916 Prosthetic socket
919 Bio-sensors
921 Bio-sensor strip
927 Data processing device
928 Sensorised socket
929 Curves
930 Bio data profile
932 Stump
1005 Virtual origin coordinate point
1006 3D surface map
1016 Socket
1029 Bio-data profile maps
1030 Bio-data profile
1031 Virtual reality vision system
1032 Residual member
1033 Liner or sock
1038 Shaping tools
1105 Virtual origin coordinate point
1106 Socket surface map
1112 Real sump origin coordinate
1129 Bio-data profile curves
1130 Bio-data profile
1132 Residual limb
1134 Handheld device
1135 Support
1138 Shaping tool

What is claimed is:

1. A method of identifying the differences in shape and the physical contact characteristics between an object and a body part which is engageable with the object comprising:
   scanning the object with radiation in order to produce a surface map of the object;
   attaching a plurality of bio-sensors to at least one of a surface of the object or to a surface of the body part at locations which are known relative to a reference point, engaging the body part with the object;
   collecting bio-sensor data from the bio-sensors to record information on the engagement between the body part and the object over the surface of the object; and
   superimposing the data from the bio-sensors over the surface map of the object in order to identify areas of the object which need to be adjusted in order to improve the fit of the body part with the object.

2. The method of claim 1, wherein the object is one of a prosthetic socket, an orthotic article, an article of furniture, or a wheelchair, and the body part is one of a stump of an amputated limb, stump of an amputated foot, a complete limb, a skin of a patient, a bottom sitting on a wheelchair, a back lying on a bed, or a liner covering at least part of the body.

3. The method according to claim 1, wherein the scanning comprises:
   projecting a radiation pattern onto the surface of the object with a radiation source at a first distance from the surface of the object;
   taking as image data an image of the radiation projected onto the surface using at least one capturing element which is in a fixed and known position relative to the radiation source;
   analyzing the image data from the capturing element to identify a position in three dimensions of each point illuminated by the projected radiation;
   varying the distance of the radiation source from the surface in order to change the parts of the surface illuminated by the projected radiation;
   using the data from the capturing element in order to identify the position of each new point illuminated by the projected radiation; and
   repeating until all points on the surface have been scanned.

4. The method according to claim 1, wherein locations of the plurality of biosensors is determined by illuminating the plurality of biosensors and capturing image data.

5. The method according to claim 1, wherein the scanning is carried out by a radiation pattern as a projected laser pattern.

6. The method according to claim 1, wherein the collecting of data comprises one of data relating to pressure or temperature at the locations.

7. The method according to claim 1, further comprising displaying a 3D model of the mapped surface to a user with the bio-sensor data superimposed thereon.

8. The method according to claim 1, further comprising projecting onto the surface of the object a pattern which is calibrated to the surface map generated by a computer so as to enable a user easily to correlate the actual surface with the virtual surface and hence easily identify on the real surface areas of the object which need adjusting based on the bio-sensor information.

9. The method according to claim 7, wherein the object is a prosthetic socket and the adjusting comprises forming an interior surface of the prosthetic socket.

10. The method according to claim 1, further comprising using data from at least one motion unit to identify areas of the object which need to be adjusted in order to improve the fit of the body part with the object during movement.

11. An apparatus for identifying the differences in shape and physical contact characteristics between an object and a body part which is engageable with the object, the apparatus comprising:
  a radiation source for scanning the surface of the object in order to produce a surface map thereof;
  an adjuster for varying at least one of a distance or orientation of the radiation source the surface of the object;
  a plurality of bio-sensors attachable to at least one of the surface of the object, to the surface of the body parts or to liners covering body parts at locations which are known relative to a reference point,
  data collectors connected to the plurality of bio-sensors for collecting bio-sensor data from the plurality of bio-sensors;
  data processing device adapted for superimposing the bio-sensor data onto the surface map to produce a bio-data profile map of the object; and
  a display for displaying the bio-data profile map to a technician.

12. The apparatus of claim 11, wherein the plurality of biosensors are arranged as a bio-sensor strip comprising plastic films, power leads and data leads, a power and data connector, wherein the plurality of bio-sensors are disposed on the bio-sensor strip (821, 921) and at least one power lead and data lead is connected to one or more of the plurality of bio-sensors and the at least one power lead and data lead are placed on the bio-sensor strip and are in contact with an interface component itself connected with a power supply and the data processing device.

13. The apparatus according to claim 11, wherein the radiation source is a conical laser assembly which comprises a single point laser and an optical element which converts the single laser beam into a two-dimensional laser array.

14. An apparatus according to claim 11, further comprising a capturing element associated with, and in a known position relative to the radiation source, the capturing element for detecting the radiation pattern on the surface and measuring the distance between a plurality of points illuminated by the radiation source and the capturing element, and a data processing device for processing the data from the capturing element and converting the data into a map of the surface.

15. An apparatus according to claim 14, wherein the capturing element is arranged in a fixed position relative to the radiation source, the distance from the laser being known, and moves with the radiation source towards and away from the surface.

16. The apparatus according to claim 11, further comprising a plurality of light sources for illuminating the surface of the object to identify locations of the plurality of biosensors.

* * * * *